US008067620B2

(12) United States Patent
Vennerstrom et al.

(10) Patent No.: US 8,067,620 B2
(45) Date of Patent: Nov. 29, 2011

(54) DISPIRO 1,2,4-TRIOXOLANE ANTIMALARIALS

(75) Inventors: Jonathan L. Vennerstrom, Omaha, NE (US); Yuxiang Dong, Omaha, NE (US); Susan A. Charman, Parkville (AU); Sergio Wittlin, Basel (CH); Jacques Chollet, Basel (CH); Darren J. Creek, Parkville (AU); Xiaofang Wang, Omaha, NE (US); Kamaraj Spiraghavan, Omaha, NE (US); Lin Zhou, Omaha, NE (US); Hugues Matile, Basel (CH); William N. Charman, Parkville (AU)

(73) Assignee: Medicines for Malaria Venture MMV, Geneva (CH)

( * ) Notice: Subject to any disclaimer, the term of this patent is extended or adjusted under 35 U.S.C. 154(b) by 340 days.

(21) Appl. No.: 11/930,606

(22) Filed: Oct. 31, 2007

(65) Prior Publication Data

US 2008/0125411 A1 May 29, 2008

Related U.S. Application Data

(63) Continuation-in-part of application No. 11/121,451, filed on May 4, 2005, now Pat. No. 7,371,778.

(51) Int. Cl.
*A61K 31/357* (2006.01)
*C07D 323/02* (2006.01)

(52) U.S. Cl. ............ 549/336; 514/462; 549/337; 544/6; 544/148; 544/374; 540/543; 546/15

(58) Field of Classification Search .................. 549/333, 549/336, 341, 337; 514/462; 544/6, 148, 544/374; 546/15; 540/543
See application file for complete search history.

(56) References Cited

U.S. PATENT DOCUMENTS

| 3,621,062 A | 11/1971 | Archer et al. |
| 3,673,222 A | 6/1972 | Archer et al. |
| 3,682,991 A | 8/1972 | Tullar et al. |
| 4,816,478 A | 3/1989 | Thomfeldt |
| 4,978,676 A | 12/1990 | Thomfeldt |
| 5,053,342 A | 10/1991 | Lawrence |
| 5,171,676 A | 12/1992 | Ziffer et al. |
| 5,216,175 A | 6/1993 | Avery et al. |
| 5,219,880 A | 6/1993 | Thomfeldt |
| 5,264,879 A | 11/1993 | Shikama |
| 5,270,344 A | 12/1993 | Herman |
| 5,430,148 A | 7/1995 | Webber et al. |
| 5,510,356 A | 4/1996 | Vennerstrom |
| 5,559,145 A | 9/1996 | Jeffort |
| 5,578,637 A | 11/1996 | Lai et al. |
| 5,614,178 A | 3/1997 | Bloom et al. |
| 5,672,624 A | 9/1997 | Posner |
| 5,721,209 A | 2/1998 | Horwitz et al. |
| 5,780,675 A | 7/1998 | Royer et al. |
| 5,817,692 A | 10/1998 | Posner |
| 5,932,591 A | 8/1999 | Posner et al. |
| 6,486,199 B1 * | 11/2002 | Vennerstrom et al. ........ 514/462 |
| 6,825,230 B2 * | 11/2004 | Vennerstrom et al. ........ 514/462 |
| 6,906,205 B2 * | 6/2005 | Vennerstrom et al. ........ 549/341 |
| 7,371,778 B2 * | 5/2008 | Vennerstrom et al. ........ 514/462 |
| 2004/0039008 A1 * | 2/2004 | Vennerstrom et al. ........ 514/278 |
| 2005/0256185 A1 * | 11/2005 | Vennerstrom et al. ........ 514/452 |

OTHER PUBLICATIONS

Online "http://www.thefreedictionary.com/analog" accessed Sep. 23, 2009.*
Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
Carlos Franco-Paredes, José Ignacio Santos-Preciado "Problem pathogens: prevention of malaria in travelers" Lancet Infectuous Diseases 2006, 6, 139-492.*
Wolff, M.E. Burger's Medicinal Chemistry 4th Ed. Part I, Wiley: New York, 1979, 336-337.*
Dong "Effect of functional group polarity on the antimalarial activity of spiro and dispiro-1,2,4-trioxolanes." Bioorganic & Medicinal Chemistry, 2006 14(18), 6368-6382.*
Posner, "Antimalarial peroxides in the qinghaosu (artemisinin) and yingzhaosu families", Exp. Opin, Ther. Patents 8 (11) 1487-1493 (1998) Ashley Publications Ltd. ISSN 1354-3776.
Jefford, "Peroxidic Antimalarials", Advances in Drug Research, vol. 29:271-323 (ISBN 0-12-013329-6) copyright 1997 Academic Press Ltd.
De Almeida Barbosa, Luiz-Claudio, "The design, synthesis and biological evaluation of stable ozonides with antimalarial activity", J.Chem. Soc., Perkin Trans. 1, 1101-1105 (1996).
De Almeida Barbosa, Luiz-Claudio, "Synthesis of some Stable Ozonides with Anti-malarial Activity", J. Chem. Soc., Perkin Trans. 1, 3251 (1992).
Vennerstrom, et al., "Dispiro-1,2,4,5-tetraoxanes: A new Class of Antimalarial Peroxides", J. Med. Chem. 35 (16):3023-3027 (1992).
Kuel, Helmut: "Uber Konstitution und Entstehung der Ozonide von Bis-adamantyliden und Bis-Bicyclo '3.3.1 non-0-yliden" Chemische Berichte, vol. 108, No. 4, 1975, pp. 1207-1217, XP002217805Tabuchi, T: "Ozonolysis of vinyl ethers in the prescence of a-diketones and a-keto esters", J. Org. Chem., vol. 56, 1991, pp. 6591-6595, XP001117555.
Dussault, P.J.: "Selectivity in Lewis acid-mediated fragmentations of peroxides and ozonides; application to the synthesis of alkenes, homoallylethers, and 1,2-dioxolanes", Perkin Trans, vol. 1, 2000, pp. 3006-3013, XP001117556.
Griesbaum, Karl, "Diozonides from Coozonolyses of Suitable O-Methyl Oximes and Ketones", Tetrahedron, Elsevier Science Publishers, Amsterdam, NL, vol. 53, No. 15, Apr. 14, 1997, pp. 5463-5470 XP004105588.

(Continued)

*Primary Examiner* — David K O Dell
(74) *Attorney, Agent, or Firm* — Baker & Daniels LLP

(57) ABSTRACT

A means and method for treating malaria, schistosomiasis, and cancer using a spiro or dispiro 1,2,4-trioxolane is described. The preferred 1,2,4-trioxolanes include a spiroadamantane group on one side of the trioxolane group, and a spirocyclohexyl on the other side of the trioxolane group. In comparison to artemisinin semisynthetic derivatives, the compounds of this invention are structurally simple, easy to synthesize, non-toxic, and potent against malarial parasites. The compounds of the invention unexpectedly provide a single-dose cure for malaria, as well as prophylactic activity against the same. The compounds are also active against schistosomiasis and cancer.

18 Claims, No Drawings

OTHER PUBLICATIONS

Meshnick, S: "Artemisinin and the Antimalarial Endoperoxides: From Herbal Remedy to Targeted Chemotherapy", Microbiological Reviews, American Society for Microbiology, Washington, D.C., US, vol. 60, No. 2, Jun. 1, 1996, pp. 301-315, XP002052313.

Stephen M. Bebge, Lyle D. Bighley and Donald C. Monkhouse "Pharmaceutical Salts" Journal of Pharmaceutical Sciences, 1977, 66, 1-19.

Wolff, Manfred E. "Burger's Medicinal Chemistry, 5ed. Part I", John Wiley and Sons, 1995, pp. 975-977.

Banker, G.S. et al. "Modern Pharmaceutics, 3ed", Marcel Dekker, New York, 1996, pp. 451 and 596.

Carlos Franco-Paredes, Jose Ignacio Santos-Preciado "Problem pathogens: prevention of malaria in travelers" Lancet Infectuous Diseases 2006, 6, 139-49.

Darren J. Creek, William N. Charman, Francis C.K. Chiu, Richard J. Prankerd, Kevin J. McCullough, Yuxiang Dong, Jonathan L. Vennerstrom, Susan A. Charman; Iron-Mediated Degradation Kinetics of Substituted Dispiro-1,2,4-trioxolane Antimalarials; Journal of Pharmaceutical Sciences, vol. 96, No. 11, 2945-2956 (Nov. 2007).

* cited by examiner

DISPIRO 1,2,4-TRIOXOLANE ANTIMALARIALS

CROSS REFERENCE TO RELATED APPLICATION

The present invention is a continuation-in-part of U.S. Ser. No. 11/121,451. The disclosures of these applications and patents are herein specifically incorporated by reference.

FIELD OF THE INVENTION

This invention relates to compositions and methods for treating malaria. Specifically, this invention relates to pharmaceutical compositions including dispiro trioxolanes, and methods of their use and manufacture.

BACKGROUND OF THE INVENTION

Malaria is an acute and often chronic infectious disease resulting from the presence of protozoan parasites within red blood cells. Caused by single-celled parasites of the genus *Plasmodium,* malaria is transmitted from person to person by the bite of female mosquitoes.

Although once prevalent in North America and other temperate regions of the world, today malaria occurs mostly in tropical and subtropic countries. Each year, between 400 million and 600 million people contract the disease, and 1.5 million to 2.7 million die of the disease.

Four species of *Plasmodium* protozoan parasites are generally responsible for malaria, including *Plasmodium vivax, Plasmodium falciparum, Plasmodium malariae,* and *Plasmodium ovale.* Of the four, *Plasmodium falciparum* is the most dangerous, accounting for half of all clinical cases of malaria and 90% of deaths from the disease.

The transmission of malaria begins when a female mosquito bites a human already infected with the malaria parasite. When the infected mosquito bites another human, sporozoites in the mosquito's saliva are transferred into the blood, which then travel to the liver. In the liver, the sporozoites divide rapidly, then enter the bloodstream where they invade red blood cells. Inside these blood cells, the merozoites multiply rapidly until they cause the red blood cells to burst, releasing into the blood stream a new generation of merozoites that then infect other red blood cells.

The symptoms associated with malaria are generally associated with the bursting of the red blood cells. The destruction of the red blood cells spills wastes, toxin, and other debris into the blood. This in turn causes an intense fever that can leave the infected individual exhausted and bedridden. More severe symptoms associated with repeat infections and/or infection by *Plasmodium falciparum* include anemia, severe headaches, convulsions, delirium and, in some instances, death.

The treatment of malaria has been especially difficult due to the ability of malaria parasites to develop resistance to drugs. Quinine, an antimalarial compound that is extracted from the bark of the South American cinchona tree, is one of the oldest and most effective pharmaceuticals in existence. The downside to quinine is that it is short-acting, and fails to prevent disease relapses. Further, quinine is associated with side effects ranging from dizziness to deafness.

Chloroquine is a synthetic chemical similar to quinine. It became the drug of choice for malaria when it was developed in the 1940s due to its effectiveness, ease of manufacture, and general lack of side effects. However, in the last few decades, malaria parasites in many areas of the world have become resistant to chloroquine.

Mefloquine is another synthetic analog of quinine that has been used in the treatment of malaria. Malaria parasites have also developed resistance to mefloquine, however. Mefloquine is also associated with undesirable central nervous side effects in some patients, including hallucinations and vivid nightmares.

Antifolate drugs are effective against malaria parasites by inhibiting their reproduction. Although the parasites have also developed a resistance to antifolate drugs, the drugs can still be used effectively in combination with other types of antimalarials. The use of combination therapies in treating malaria has the drawbacks of being inconvenient and expensive, however.

More recent developments in the treatment of malaria have involved the use of the peroxide functional group, as exemplified by the drug artemisinin, which contains a unique 1,2,4-trioxane heterocyclic pharmacophore. The antimalarial action of artemisinin is thought to be due to its reaction with the iron in free heme molecules in the malaria parasite with the generation of free radicals leading to cellular destruction.

The discovery of artemisinin (qinghaosu), a naturally occurring endoperoxide sesquiterpene lactone (Meshnick et al., 1996; Vroman et al. 1999; Dhingra et al., 2000) initiated a substantial effort to elucidate its molecular mechanism of action (Jefford, 1997; Cumming et al., 1997) and to identify novel antimalarial peroxides (Dong and Vennerstrom, 2001). Many synthetic 1,2,4-trioxanes, 1,2,4,5-tetraoxanes, and other endoperoxides have been prepared.

Although the clinically useful semisynthetic artemisinin derivatives are rapid acting and potent antimalarial drugs, they have several disadvantages including recrudescence, neurotoxicity, (Wesche et al., 1994) and metabolic instability (White, 1994). A fair number of these compounds are quite active in vitro, but most suffer from low oral activity. (White, 1994; van Agtmael et al., 1999). Although many synthetic antimalarial 1,2,4-trioxanes have since been prepared (Cumming et al., 1996; Jefford, 1997), there exists a need in the art to identify new peroxide antimalarial agents, especially those which are easily synthesized, are devoid of neurotoxicity, and which possess improved pharmacokinetic properties, e.g. improved stability, oral absorption, etc.

SUMMARY OF THE INVENTION

The invention describes a method and composition for treating malaria with dispiro 1,2,4-trioxolanes, their prodrugs and analogues. With a few exceptions, preferred trioxolanes of this invention contain a cis-8'-phenyl substituent on the cyclohexyl ring. The compounds of the invention fall into one of following three structural classes:

The first class:

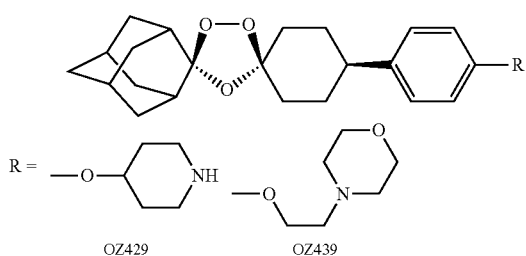

OZ429  OZ439

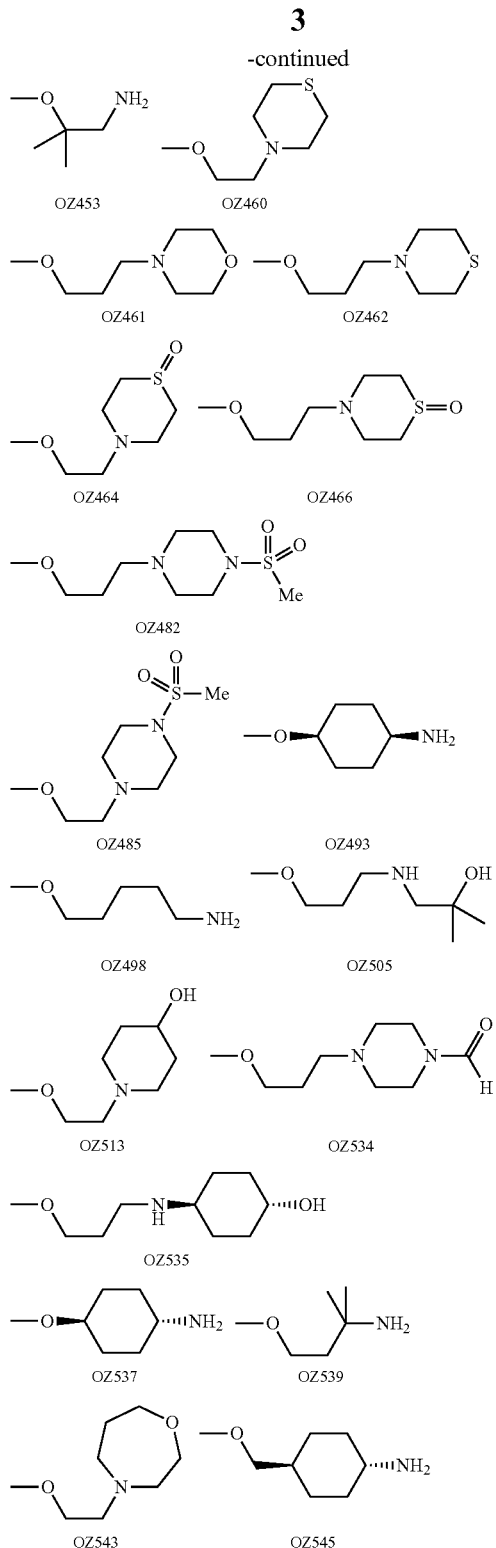

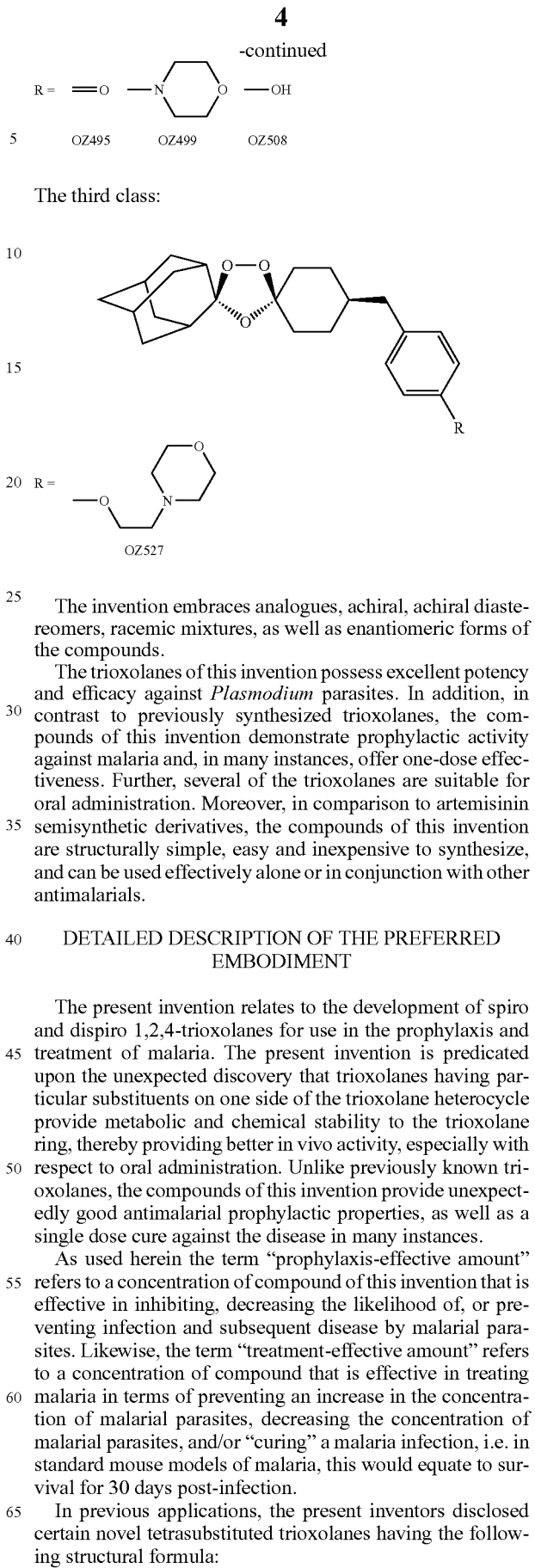

The invention embraces analogues, achiral, achiral diastereomers, racemic mixtures, as well as enantiomeric forms of the compounds.

The trioxolanes of this invention possess excellent potency and efficacy against *Plasmodium* parasites. In addition, in contrast to previously synthesized trioxolanes, the compounds of this invention demonstrate prophylactic activity against malaria and, in many instances, offer one-dose effectiveness. Further, several of the trioxolanes are suitable for oral administration. Moreover, in comparison to artemisinin semisynthetic derivatives, the compounds of this invention are structurally simple, easy and inexpensive to synthesize, and can be used effectively alone or in conjunction with other antimalarials.

DETAILED DESCRIPTION OF THE PREFERRED EMBODIMENT

The present invention relates to the development of spiro and dispiro 1,2,4-trioxolanes for use in the prophylaxis and treatment of malaria. The present invention is predicated upon the unexpected discovery that trioxolanes having particular substituents on one side of the trioxolane heterocycle provide metabolic and chemical stability to the trioxolane ring, thereby providing better in vivo activity, especially with respect to oral administration. Unlike previously known trioxolanes, the compounds of this invention provide unexpectedly good antimalarial prophylactic properties, as well as a single dose cure against the disease in many instances.

As used herein the term "prophylaxis-effective amount" refers to a concentration of compound of this invention that is effective in inhibiting, decreasing the likelihood of, or preventing infection and subsequent disease by malarial parasites. Likewise, the term "treatment-effective amount" refers to a concentration of compound that is effective in treating malaria in terms of preventing an increase in the concentration of malarial parasites, decreasing the concentration of malarial parasites, and/or "curing" a malaria infection, i.e. in standard mouse models of malaria, this would equate to survival for 30 days post-infection.

In previous applications, the present inventors disclosed certain novel tetrasubstituted trioxolanes having the following structural formula:

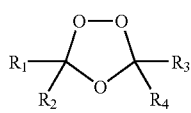

wherein $R_1$, $R_2$, $R_3$, and $R_4$ represent combinations of ring systems, acyclic systems, and functional groups that provide sufficient steric hindrance about the trioxolane ring in order to give the ring chemical and metabolic stability.

The trioxolane compounds of the present invention are surprisingly iron-stable, and have been found to provide unexpectedly good antimalarial activity. Compounds of this structure are orally active, and certain representative compounds have even been found to be malaria-curative with a single dose. Furthermore, the preferred compounds of this invention have an improved safety profile in comparison to previously disclosed trioxolane compounds.

In one embodiment of the invention, the compounds have the following general structure, with the R groups listed below the main structure. "OZ" (which stands for "ozonide") is an internal designation for these compounds that will be used throughout the remainder of the application for convenience.

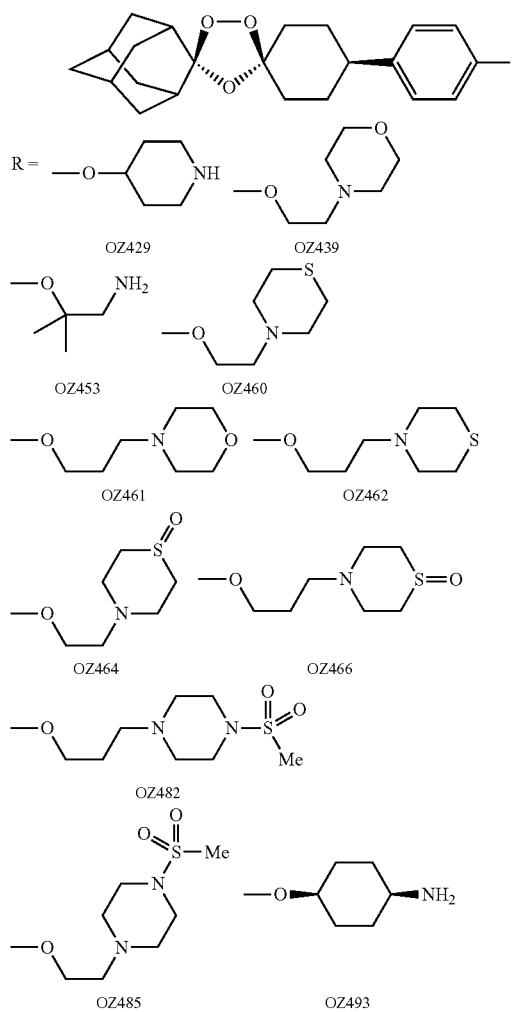

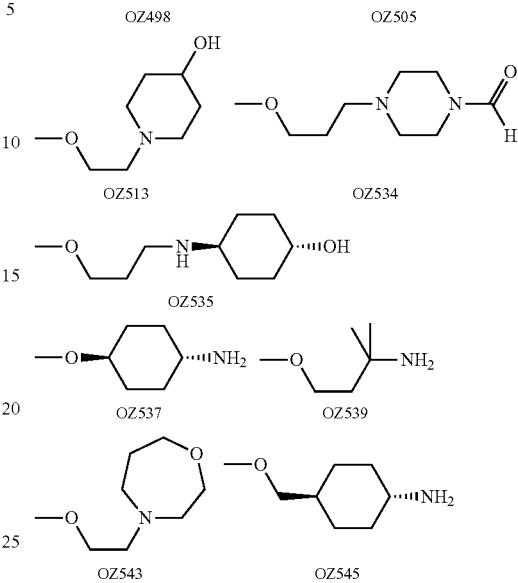

In a second embodiment of the invention, the compounds have the following structure:

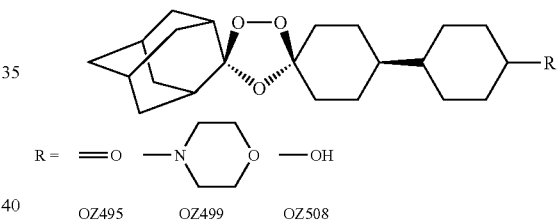

In a third embodiment of the invention, the compounds have the following structure:

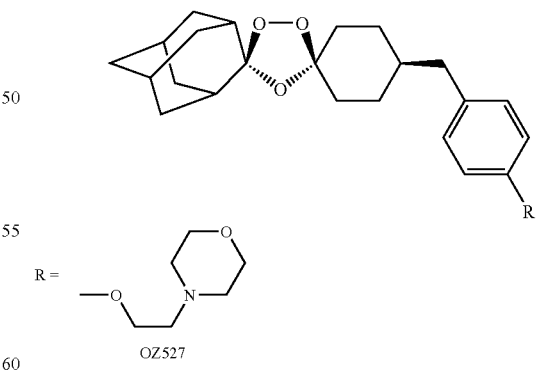

Preferred compounds of the present invention identified thus far include:

-cis-adamantane-2-spiro-3'-8'-[4'-[2'-(4'-morpholinyl) ethoxy]phenyl]-1',2',4'-trioxaspiro[4.5]decane mesylate (OZ439);

-cis-Adamantane-2-spiro-3'-8'-[4'-[3'-(4'-morpholinyl)propoxy]phenyl]-1',2',4'-trioxaspiro[4.5]decane mesylate (OZ461);

-cis-Adamantane-2-spiro-3'-8'-[4'-[3'-(4'-thiomorpholinyl)propoxy]phenyl]-1',2',4'-trioxaspiro[4.5]decane mesylate (OZ462);

-cis-Adamantane-2-spiro-3'-8'-[4'-[3'-(1'-oxido-4'-morpholinyl)propoxy]phenyl]-1',2',4'-trioxaspiro[4.5]decane mesylate (OZ466);

-cis-Adamantane-2-spiro-3'-8'-[4'-[3'-[4'-(methylsulfonyl)-1'-piperazinyl]propoxy]phenyl]-1',2',4'-trioxaspiro[4.5]decane p-tosylate (OZ482);

-cis-Adamantane-2-spiro-3'-8'-[4'-(cis-4'-aminocyclohexyloxy)phenyl]-1',2',4'-trioxaspiro[4.5]decane mesylate (OZ493);

-cis-Adamantane-2-spiro-3'-8'-[4'-(4'-morpholinyl)cyclohexyl]-1',2',4'-trioxaspiro[4.5]decane mesylate (OZ499);

-cis-Adamantane-2-spiro-3'-8'-(4'-hydroxycyclohexyl)-1',2',4'-trioxaspiro[4.5]decane (OZ508);

-cis-Adamantane-2-spiro-3'-8'-[[4'-[2'-(4'-morpholinyl)ethoxy]phenyl]methyl]-1',2',4'-trioxaspiro[4.5]decane p-tosylate (OZ527);

-cis-Adamantane-2-spiro-3'-8'-[4'-(trans-4'-aminocyclohexyloxy)phenyl]-1',2',4'-trioxaspiro[4.5]decane mesylate (OZ537);

-cis-Adamantane-2-spiro-3'-8'-[4'-(3'-amino-3'-methylbutoxy)phenyl]-1',2',4'-trioxaspiro[4.5]decane p-tosylate (OZ539);

-cis-Adamantane-2-spiro-3'-8'-[4'-[2'-(tetrahydro-1',4'-oxazepin-4'(5'H)-yl)ethoxy]phenyl]-1',2',4'-trioxaspiro[4.5]decane p-tosylate (OZ543); and -cis-Adamantane-2-spiro-3'-8'-[4'-[(trans-4'-aminocyclohexyl)methoxy]phenyl]-1',2',4'-trioxaspiro[4.5]decane mesylate (OZ545).

The most preferred of these compounds are OZ439, OZ466, OZ493, OZ527, OZ537, and OZ539 as they have been found to be malaria-curative in some instances with a single dose.

Notable features of these spiro and dispiro 1,2,4-trioxolanes in comparison to the artemisinin semisynthetic derivatives are their structural simplicity and ease of synthesis. For example, dispiro trioxolanes may be easily synthesized by the coozonolysis of the O-methyl oximes of cycloalkanones in the presence of the requisite cycloalkanone derivatives according to the method of Griesbaum et al. (1997a; 1997b) as illustrated below for the symmetrical dispiro cyclohexyl trioxolane:

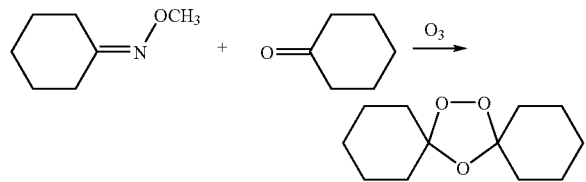

If yields are low in this coozonolysis reaction, yields can improve dramatically when the O-methyloxime and ketone are "reversed." This novel procedure provides a uniquely convenient method to synthesize spiro and dispiro trioxolanes. Advantages of the oxime ether route over the alkene approach include convenient synthesis of starting materials (oxime ethers vs. tetrasubstituted alkenes), higher yield and selectivity of formation of desired trioxolanes by the judicious selection of paired reaction substrates.

The trioxolanes may be purified by crystallization or by flash column chromatography. Their structures and purity may be confirmed by analytical HPLC, $^1$H and $^{13}$C NMR, IR, melting point and elemental analysis.

Formation of a trioxolane from an oxime ether and a ketone is presumed to be a three-step process. The sequence begins by the electrophilic addition of ozone to the oxime double bond to form a primary ozonide. Second, the very unstable primary adduct fragments to a reactive carbonyl oxide driven in part by the concomitant expulsion of the relatively stable methyl nitrite. Third, the carbonyl oxide undergoes a [3+2] cycloaddition with a ketone to give the secondary ozonide or 1,2,4-trioxolane. It remains to be

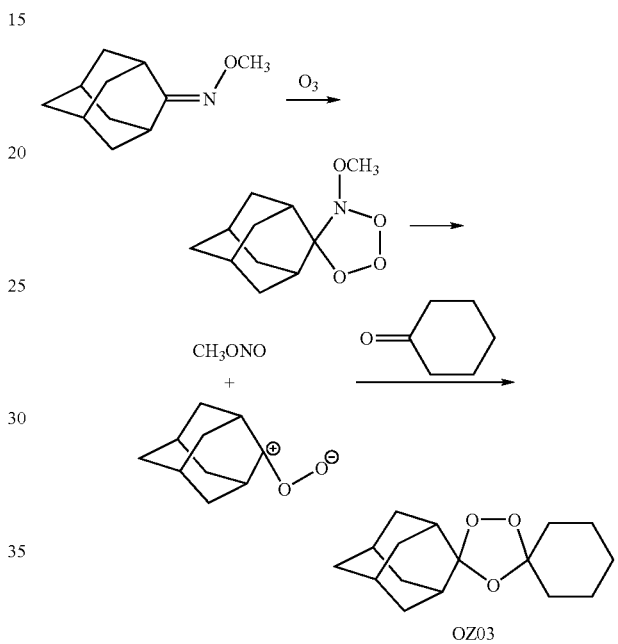

determined whether this is a stepwise or a concerted recombination process.

Most of the new dispiro trioxolanes contain a spiroadamantane and can be synthesized by the coozonolysis of adamantanone O-methyl oxime in the presence of the requisite cycloalkanone derivative. The preferred reaction solvents for the coozonolysis reactions are hydrocarbon solvents such as pentane or cyclohexane; more polar solvents tend to decrease the yield of the reaction. When ketones are not readily soluble in pentane or cyclohexane, a mixed solvent (pentane/methylene chloride) or methylene chloride alone may be used. Several factors govern the ratio of oxime ether to ketone. In some reactions, in order to avoid diperoxide (1,2,4,5-tetraoxane) formation, to preclude diozonide formation from diketones, and to promote the reaction with readily pentane soluble ketones, excess ketone (2:1) is used. Most commonly in the discovery synthesis stage, and especially in cases where ketones are not readily soluble in pentane, expensive, or difficult to remove in the reaction workup, a 1:1 ratio of ketone to oxime ether may be used. In large scale trioxolane syntheses, a 1.5-fold excess of oxime ether can be used to achieve higher conversions of ketones into the desired product trioxolanes without causing purification problems.

The dispiro trioxolane compositions of the present invention may be generally used for the prophylaxis and treatment of malaria. The trioxolane compositions of the present invention are administered along with a pharmaceutically acceptable carrier. Any pharmaceutically acceptable carrier may be generally used for this purpose, provided that the carrier does not significantly interfere with the stability or bioavailability of the trioxolane compounds of this invention.

The trioxolanes of this invention can be administered in any effectively pharmaceutically acceptable form to warm blooded animals, including human and other animal subjects, e.g. in topical, lavage, oral, suppository, parenteral, or infusible dosage forms, as a topical, buccal, sublingual, or nasal spray or in any other manner effective to deliver the agents. The route of administration will preferably be designed to optimize delivery and/or localization of the agents to target cells.

In addition to the active compounds i.e. the trioxolanes, the pharmaceutical compositions of this invention may contain suitable excipients and auxiliaries which facilitate processing of the active compounds into preparations which can be used pharmaceutically. Oral dosage forms encompass tablets, capsules, and granules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, dragee-making, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Oral dosage forms may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, including for example, sodium carboxymethyl cellulose, sorbitol and/or dextran. Such compositions may also comprise adjuvants such as preserving, wetting, emulsifying, and dispensing agents. They may also be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

In addition to administration with conventional carriers, active ingredients may be administered by a variety of specialized delivery drug techniques which are known to those of skill in the art, such as portable infusion pumps.

The trioxolane compositions of the present invention are administered along with a pharmaceutically acceptable carrier in an amount sufficient to prevent malarial infection and/or treat an active infection. The trioxolane compounds of this invention have extremely low toxicity and a low degree of side effects even at high doses. The dosing range of the trioxolane compositions will vary depending on a number of factors, such as whether it is used for prophylaxis or treatment of an active infection, route of administration, dosing schedule, etc. In general, the therapeutic dose of trioxolane may range between about 0.1-1000 mg/kg/day, with between about 1-100 mg/kg/day being preferred. The foregoing doses may be administered as a single dose or may be divided into multiple doses for administration. For single dosing, a possible dosing range is from about 0.5-5.0 mg/kg. However, this dosing range may extend much higher.

The trioxolane compositions may be administered once to several times daily. For malaria prevention, a typical dosing schedule could be, for example (other than for single dose cure), 2.0-1000 mg/kg weekly beginning 1-2 weeks prior to malaria exposure taken up until 1-2 weeks post-exposure.

The spiro and dispiro trioxolanes of this invention may be administered as any pharmaceutically effective salt form. Such salts are well known in the art and include, but are not limited to acetate, adipate, alginate, citrate, aspartate, benzoate, benzene sulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluene sulfonate and undecanoate salts. Preferred salts are those that increase the bioavailability of the trioxolane compounds. This will depend upon a number of factors, including the chemical structure of the trioxolane, the carrier to which it is incorporated, the route of administration, etc.

As a general rule, it is preferred to administer the compounds of the present invention, as well as other antimalarials, as part of a combination therapy in order to prevent resistance. The benefits of such combination therapy in treating malaria are well known in the art. Combination therapy with antimalarial drugs is the simultaneous use of two or more blood schizontocidal drugs with independent modes of action and different biochemical targets in the parasite. The concept of combination therapy is based on the synergistic or additive potential of two or more drugs, to improve therapeutic efficacy and also delay the development of resistance to the individual components of the combination. Examples of current antimalarial drug combinations include artemisinin combinations with chloroquine and mefloquine and quinine based combinations with tetracycline and clindamycin. The trioxolanes of the present invention are expected to be administered in combinations with various other antimalarials including, but not limited to, artemether, chloroquine, mefloquine, piperaquine, and pyronaridine.

The spiro and dispiro trioxolanes of this invention have been found to be effective in the treatment of schistosomiasis. Schistosomiasis ranks second behind malaria in terms of socioeconomic and public health importance in tropical and subtropical areas. The disease is endemic in 74 developing countries, infecting more than 200 million people in rural agricultural and peri-urban areas. An estimated 500-600 million people worldwide are at risk from the disease.

The major forms of human schistosomiasis are caused by five species of water-borne flatworm, or blood flukes, called schistosomes. One of these species is *Schistosoma mansoni*, which has been reported in 53 countries in Africa, the Eastern Mediterranean, the Caribbean, and South America. The parasites enter the body through contact with infested surface water, primarily among people engaged in agriculture and fishing. The parasites normally infect the host during the cercaria, or larval stage. Once inside the host, the cercaria develop into adults or schistosomes.

Current treatments for schistosomiasis have focused primarily on prophylaxis, i.e. prevention of host infection by cercaria. Currently, praziquantel is the most widely used drug for treatment of schistosomiasis. While artemether has demonstrated activity in the prophylaxis of schistosomiasis, it has not shown any activity against adult *S. mansoni*.

It has now been unexpectedly discovered that the spiro and dispiro trioxolanes of this invention are active against both cercaria and adult *S. mansoni*, *S. japonicum* when administered in the dosages and manner outlined above with respect to treatment of malarial parasites. It is also believed the trioxolanes of this invention will be active against *S. haematobium*. Preferred dosing levels of the dispiro trioxolanes of this invention are about 100-200 mg/kg/day orally.

Other drugs besides trioxolanes which are compatible with the carrier ingredients may also be incorporated into the carrier. Such drugs may be readily ascertained by those of ordinary skill in the art and may include, for instance, antibiotics, other antimalarials, antiinflammatory agents, etc.

It is understood that the present invention contemplates the use of not only the above-stated trioxolane compounds themselves, but their prodrugs which metabolize to the compound and the analogues and biologically active salt forms thereof, as well as optical isomers which provide the same pharmaceutical results.

The following examples are offered to illustrate but not limit the invention. Thus, they are presented with the understanding that various formulation modifications as well as method of delivery modifications may be made and still be within the spirit of the invention.

EXAMPLE 1

Antimalarial Activity

Activity of 1,2,4-trioxolanes against *P. falciparum* in vitro. Each trioxolane was screened against the chloroquine-resistant K1 and chloroquine-sensitive NF54 strains of *Plasmodium falciparum* in vitro.

Activity of 1,2,4-trioxolanes against *P. berghei* in vivo. In the single dose in vivo screen, NMRI mice infected with the ANKA strain of *P. berghei* (groups of five mice) were treated one day post-infection with trioxolanes dissolved or suspended in standard suspending vehicle (SSV). The SSV consists of either 0.5% w/v carboxymethyl cellulose, 0.5% v/v benzyl alcohol, 0.4% v/v Tween 80, and 0.9% w/v sodium chloride in water or 0.5% hydroxypropylmethylcellulose 0.4% v/s Tween 80, and 0.5% v/v benzyl alcohol in water. Trioxolanes were administered as single po 30 mg/kg doses. Antimalarial activity was measured by percent reduction in parasitemia on day three post-infection and survival times compared to an untreated control group. Survival to day 30 post-infection is considered to be a cure in this model.

Comparative data for the antimalarial drug controls artesunate (AS), artemether (AM), chloroquine (CQ), and mefloquine (MQ) are also included.

TABLE 1

Antimalarial activity of trioxolanes against
*P. falciparum* in vitro and *P. berghei* in vivo.

| Compd | $IC_{50}$ (ng/ml) K1/NF54 | Activity (%) 30 mg/kg SSV po | Survival (days) 30 mg/kg SSV po | Cures 30 mg/kg SSV po |
|---|---|---|---|---|
| Control | — | 0 | 6-7 | — |
| OZ429 | 0.52/1.3 | 99.97 | 27.8 | 4/5 |
| OZ439 | 1.5/2.0 | 98 | >30 | 5/5 |
| OZ453 | 0.66/1.1 | >99.9 | 24.0 | 3/5 |
| OZ460 | 3.5/3.3 | 99 | 25.0 | 3/5 |
| OZ461 | 2.8/2.8 | 99.8 | >30 | 5/5 |
| OZ462 | 3.2/3.1 | 99.7 | >30 | 5/5 |
| OZ464 | 3.5/3.3 | 99.8 | >30 | 5/5 |
| OZ466 | 3.2/2.5 | >99.9 | >30 | 5/5 |
| OZ482 | 4.2/4.3 | 99.9 | >30 | 5/5 |
| OZ485 | 6.1/5.6 | 99.9 | 24.8 | 2/5 |
| OZ493 | 1.1/2.1 | 99.7 | >30 | 5/5 |
| OZ495 | 1.9/3.8 | 99.3 | 26.8 | 3/5 |
| OZ498 | 1.6/2.5 | 99.0 | 24.8 | 2/5 |
| OZ499 | 1.0/1.5 | 99.8 | 25.2 | 1/5 |
| OZ505 | 2.1/1.9 | 99.7 | 27.4 | 4/5 |
| OZ508 | 1.2/1.4 | 99.8 | 24.4 | 3/5 |
| OZ513 | 1.1/0.82 | 99.9 | 21.0 | 1/5 |
| OZ527 | 3.6/2.9 | 99.7 | >30 | 5/5 |
| OZ534 | 2.1/1.7 | 99.8 | 22.8 | 1/5 |
| OZ535 | 1.8/1.6 | 99.7 | 26.4 | 3/5 |
| OZ537 | 2.1/2.4 | 99.9 | >30 | 5/5 |
| OZ539 | 1.5/1.4 | 99.7 | 25.2 | 3/5 |
| OZ543 | 1.3/2.2 | 99.6 | >30 | 5/5 |
| OZ545 | 3.3/3.9 | 99.5 | 27.6 | 4/5 |
| OZ277 | 1.0/0.91 | 99.7 | 8.0 | 0/5 |
| OZ401 | 1.9/1.7 | 98 | 23.7 | 3/5 |
| AS | 1.3/1.6 | 92 | 9.0 | 0/5 |
| AM | 0.74/1.2 | 99.7 | 9.0 | 0/5 |
| CQ | 62/5.1 | 99.9 | 9.6 | 0/5 |
| MQ | 3.0/5.8 | 99.6 | 21.8 | 0/5 |

The data in Table 1 demonstrate unexpected single-dose curative properties of these new trioxanes in the *P. berghei*-infected mouse model. In these experiments, compounds were administered orally in the SSV vehicle at single 30 mg/kg doses 24 h after infection. Compared to OZ277 (described in the inventors' earlier patent) and all of the control antimalarial drugs, these new trioxolanes cured 1/5 to 5/5 of the infected mice.

OZ439, OZ461, OZ462, OZ464, OZ466, OZ482, OZ493, OZ527, and OZ537 successfully cured the disease in all five of its recipients.

EXAMPLE 2

Effectiveness of Selected OZ Compounds in the Treatment and Prophylaxis of Malarial Infections Prophylactic activity of 1,2,4-trioxolanes against *P. berghei* in vivo: Compounds were dosed orally to mice in the SSV vehicle described in Example 1. Compounds were administered as a single 100 mg/kg oral dose administered 48, 72 or 96 h prior to infection or as a single 30 mg/kg oral dose 24 h prior to infection. All groups (n=5 mice per group) including an untreated control group, were infected at the same time and parasitemia was determined for each animal on day 3 post-infection and compared with the level of parasitemia in control animals.

TABLE 2

Prophylactic activity of selected trioxolanes given 24 or 48 h prior to infection in *P. berghei*-infected mice

| Compound | 48 h prior to infection (100 mg/kg) | | 24 h prior to infection (30 mg/kg) | |
|---|---|---|---|---|
| | Activity (%) | Cures | Activity (%) | Cures |
| OZ429 | 99.8 | 5/5 | 99.8 | 2/5 |
| OZ439 | 99.6 | 5/5 | 99.8 | 5/5 |
| OZ453 | 99.7 | 5/5 | 99.9 | 0/5 |
| OZ460 | 99.6 | 5/5 | 99.8 | 3/5 |
| OZ461 | 99.7 | 5/5 | 99.9 | 5/5 |
| OZ462 | 99.7 | 5/5 | 99.8 | 5/5 |
| OZ464 | 99.7 | 5/5 | 99.9 | 3/5 |
| OZ466 | 99.7 | 5/5 | 99.8 | 5/5 |
| OZ482 | >99.9 | 5/5 | >99.9 | 3/5 |
| OZ485 | >99.9 | 5/5 | >99.9 | 3/5 |
| OZ493 | 99 | 5/5 | >99.9 | 3/5 |
| OZ495 | >99.9 | 0/5 | >99.9 | 1/5 |
| OZ498 | 99.8 | 5/5 | 99.8 | 4/5 |
| OZ499 | 99.6 | 5/5 | 99.8 | 5/5 |
| OZ505 | 99.5 | 5/5 | >99.9 | 2/5 |
| OZ508 | 99.8 | 4/5 | 99.7 | 4/5 |
| OZ513 | 99.7 | 5/5 | 99.9 | 1/5 |
| OZ527 | 99 | 5/5 | 99.4 | 5/5 |
| OZ534 | >99.9 | 5/5 | >99.9 | 1/5 |
| OZ535 | >99.9 | 5/5 | >99.9 | 0/5 |
| OZ537 | >99.9 | 5/5 | >99.9 | 5/5 |
| OZ539 | >99.9 | 5/5 | >99.9 | 4/5 |
| OZ277 | 0 | 0/5 | 13 | 0/5 |
| OZ323 | 99.5 | 5/5 | 99.7 | 0/5 |
| OZ401 | 99.6 | 5/5 | 99.8 | 1/5 |
| artesunate | 0 | 0/5 | 21 | 0/5 |
| chloroquine | 57 | 0/5 | 37 | 0/5 |
| mefloquine | 99.9 | 3/5 | >99.9 | 3/5 |

TABLE 3

Prophylactic activity of selected trioxolanes given 72 or 96 h prior to infection in *P. berghei*-infected mice

| Compound | 72 h prior to infection (100 mg/kg) | | 96 h prior to infection (100 mg/kg) | |
|---|---|---|---|---|
| | Activity (%) | Cures | Activity (%) | Cures |
| OZ439 | 99.6 | 5/5 | 99.5 | 5/5 |
| OZ461 | 99.6 | 5/5 | 99.4 | 4/5 |
| OZ462 | 99.6 | 5/5 | 99.6 | 3/5 |
| OZ466 | 99.2 | 5/5 | 99.1 | 5/5 |
| OZ482 | 99.6 | 4/5 | 99.6 | 3/5 |
| OZ493 | 99.9 | 5/5 | 99.5 | 3/5 |
| OZ323 | >99.9 | 1/5 | 90 | 0/5 |
| OZ401 | 99.6 | 3/5 | 99.5 | 0/5 |
| mefloquine | >99.9 | 0/5 | ND | ND |

As demonstrated by the data in Tables 2 and 3, the present inventors discovered an unexpected prophylaxis potential of these new trioxolanes. Compared to some of the more active trioxolanes (OZ277, OZ323, OZ401) described in earlier patent applications, some of the newer trioxolanes had prophylaxis properties superior to those of the control antimalarial drugs, even exceeding that of mefloquine, a drug known for its powerful prophylactic properties.

Blood stability studies: Compounds were incubated at 37° C. in freshly collected rat blood. At selected time points, duplicate aliquots of the whole blood were sampled, centrifuged and the plasma assayed for parent compound by LC-MS.

Pharmacokinetic studies in rats: Compounds were administered orally to rats (n=2) at a dose of 10 mg/kg in a suspension formulation containing hydroxypropylmethyl cellulose, Tween 80, benzyl alcohol, and water. Blood samples were taken periodically over 48 h, centrifuged immediately following collection, and plasma was assayed for parent compound by LC-MS. Oral bioavailability for each compound was calculated relative to an IV dose for each compound in a suitable vehicle.

TABLE 4

Pharmacokinetic properties of selected trioxolanes in rats

| Compound | Stability in Rat Blood ($t_{1/2}$) at 37° C. | In Vivo Oral $t_{1/2}$ at 10 mg/kg (h) | Oral Bioavailability at 10 mg/kg (%) |
|---|---|---|---|
| OZ209 | 0.8 | 1.2 | 12 |
| OZ277 | 0.8 | 1.6 | 19 |
| OZ323 | 7.7 | 5.2 | 100 |
| OZ401 | 5.7 | 5.3 | 80 |
| OZ429 | 5.5 | 5.3 | 73 |
| OZ439 | 13 | 15.2 | 94 |
| OZ453 | 6.1 | not evaluated in vivo | |
| OZ461 | >17 | 14 | 71 |
| OZ462 | >17 | 1.2 | 35 |
| OZ466 | >17 | 2.6 | 90 |
| OZ482 | >17 | 9.6 | 100 |
| OZ493 | >17 | 7.7 | 51 |
| OZ527 | 5 | 15.4 | 66 |
| OZ537 | >17 | 11.8 | 29 |

Data in Table 4 show that trioxolanes containing the cis-8'-phenyl substituent on the cyclohexyl ring demonstrated surprisingly improved stability in rat blood at 37° C. in comparison to the earlier compounds containing a cis-8'-alkyl substituent. With the exception of OZ462, which was found to be metabolically unstable, all of the cis-8'-phenyl compounds tested had considerably longer half-lives in rats following oral administration, and correspondingly higher oral bioavailabilities, in comparison to compounds containing the cis-8'-alkyl substituent.

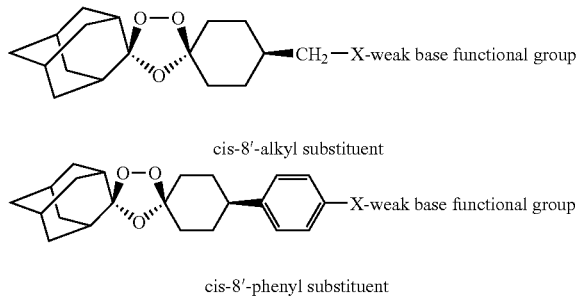

cis-8'-alkyl substituent cis-8'-phenyl substituent

EXAMPLE 3

Preferred Procedures for Preparation of Compounds

The following describes preferred synthesis methods for the compounds of the present invention. In some instances, the inventors' previous OZ compounds are referenced, the subject matter of which is disclosed in one or more of U.S. Pat. Nos. 6,486,199, 6,825,230, and 6,906,205, as well as the parent application Ser. No. 11/121,451, the disclosures of which are all specifically incorporated by reference.

cis-Adamantane-2-spiro-3'-8'-[4'-(4'-piperidinyloxy)phenyl]-1',2',4'-trioxaspiro[4.5]decane mesylate (OZ429). To a solution of OZ288 (1.426 g, 4 mmol), 1-Boc-4-hydroxypiperidine (0.966 g, 4.8 mmol), and triphenylphosphine (2.10 g, 8 mmol) in THF (50 ml) at rt was added DIPAD (1.618 g, 8 mmol) dropwise. The reaction mixture was stirred at rt for 72 h and concentrated. The residue was crystallized from ethanol (30 ml) containing triethylamine (404 mg) to give the Boc-protected trioxolane intermediate. To a methanesulfonic acid solution in TBF (1.5 M, 12 ml) was added the above intermediate. The mixture was stirred at rt for 24 h before it was diluted with ether (100 ml). The resulting precipitate was collected by filtration, washed with ether (100 ml) and EtOAc (50 ml), and dried to give trioxolane OZ429 (0.79 g, 37%) as a white solid. mp 148-150° C.; $^1$H NMR (500 MHz, CDCl$_3$) δ 1.61-2.29 (m, 26H), 2.44-2.53 (m, 1H), 2.81 (s, 3H), 3.21-3.45 (m, 4H), 4.58 (s, 1H), 6.81 (d, J=8.8 Hz, 2H), 7.12 (d, J=8.8 Hz, 2H), 8.65 (brs, 1H), 8.86 (brs, 1H); $^{13}$C NMR (125.7 MHz, CDCl$_3$) δ 26.48, 26.68, 26.89, 31.59, 34.71, 34.81, 36.41, 36.80, 39.33, 39.96, 42.06, 67.72, 108.36, 111.40, 115.88, 127.94, 139.50, 154.66. Anal. Calcd for C$_{28}$H$_{41}$NO$_7$S: C, 62.78; H, 7.71; N, 2.61. Found: C, 62.94; H, 7.63; N, 2.75.

cis-Adamantane-2-spiro-3'-8'-[4'-[2'-(4'-morpholinyl)ethoxy]phenyl]-1',2',4'-trioxaspiro[4.5]decane mesylate (OZ439). To a solution of OZ288 (1.0 g, 2.81 mmol) in dry acetonitrile (50 ml) were added powdered NaOH (0.45 g, 11.23 mmol) and tetrabutylammonium hydrogen sulfate (0.19 g, 0.562 mmol). The mixture was stirred at 25° C. for 30 min before N-(2-chloroethyl)morpholine hydrochloride (1.05 g, 5.62 mmol) was added. After the addition, it was stirred at 60° C. overnight. The inorganic solid was filtered off and washed with CH$_2$Cl$_2$. After removal of the solvents, the residue was dissolved in EtOAc (50 ml). The organic layer was washed with water and brine and dried over MgSO$_4$. Removal of the solvent afforded the free base as a colorless solid. To the solution of the above free base in CH$_2$Cl$_2$ (10 ml) at 0° C. was added dropwise a solution of methanesulfonic acid (0.216 g, 2.25 mmol) in ether (10 ml). The solid obtained was filtered, washed with ether (25 ml), and dried under vacuum at 40° C. to afford trioxolane OZ439 (1.09 g, 78%) as a colorless solid. mp 152-154° C.; $^1$H NMR (500 MHz, CDCl$_3$) δ 1.61-2.11 (m, 22H), 2.46-2.56 (m, 1H), 2.81 (s, 3H), 3.09 (brs, 2H), 3.52-3.56 (m, 2H), 3.61-3.68 (m, 2H), 3.97-4.19 (m, 4H), 4.45-4.50 (m, 2H), 6.84 (d, J=8.8 Hz, 2H), 7.14 (d, J=8.8 Hz, 2H), 11.74 (brs, 1H); $^{13}$C NMR (125.7 MHz, CDCl$_3$) δ 26.43, 26.83, 31.54, 34.63, 34.75, 36.36, 36.75, 39.37, 41.98, 52.85, 56.74, 62.81, 63.79, 108.28, 111.38, 114.43, 127.94, 139.96, 155.34. Anal. Calcd for C$_{29}$H$_{43}$NO$_8$S: C, 61.57; H, 7.66; N, 2.48. Found: C, 61.80; H, 7.48; N, 2.48.

cis-Adamantane-2-spiro-3'-8'-[4'-(2'-amino-1',1'-dimethylethoxy)phenyl]-1',2',4'-trioxaspiro[4.5]decane mesylate (OZ453). Step 1. Diisopropyl azodicarboxylate (0.36 ml, 1.83 mmol) was added dropwise to a mixture of OZ450 (0.31 g, 0.72 mmol), phthalimide (0.22 g, 1.49 mmol), and triphenylphosphine (0.48 g, 1.83 mmol) in THF (12 ml) at 0° C. under N$_2$. The resulting mixture was stirred at rt for 2 d and then quenched with 5% aq. NaHCO$_3$ (10 ml). The solid was collected by filtration and washed with water, THF, and ether to afford the phthalimido intermediate (0.30 g, 75%) as a colorless solid. mp 162-163° C. $^1$H NMR (500 MHz, CDCl$_3$) δ 1.31 (s, 6H), 1.60-2.08 (m, 22H), 2.46-2.56 (m, 1H), 3.94 (s, 2H), 6.92 (d, J=8.5 Hz, 2H), 7.06 (d, J=8.5 Hz, 2H), 7.70-7.76 (m, 2H), 7.85-7.91 (m, 2H). Step 2. A mixture of the above phthalimido intermediate (0.21 g, 0.38 mmol) and hydrazine monohydrate (1.0 ml) in chloroform (20 ml) and methanol (3 ml) was heated at 50° C. for 24 h. The reaction mixture was cooled to rt, filtered to remove the solid by-product, and concentrated. The residue was dissolved in CH$_2$Cl$_2$ (30 ml), washed with water and brine, dried over MgSO$_4$, filtered, and concentrated. The residue was dissolved in CH$_2$Cl$_2$ (5 ml) and then the solution of methanesulfonic acid (40 mg, 0.42 mmol) in ether (20 ml) was added. The precipitate was collected by filtration to afford trioxolane OZ453 (0.15 g, 75%) as a colorless solid. mp 146-148° C.; $^1$H NMR (500 MHz, DMSO-d$_6$) δ 1.25 (s, 6H), 1.47-1.62 (m, 2H), 1.63-1.99 (m, 20H), 2.31 (s, 3H), 2.47-2.67 (m, 1H), 3.04 (q, J=5.8 Hz, 2H), 6.97 (d, J=8.3 Hz, 2H), 7.17 (d, J=8.3 Hz, 2H), 7.94 (brs, 3H); $^{13}$C NMR (125.7 MHz, DMSO-d$_6$) δ 23.95, 25.98, 26.39, 31.33, 34.26, 34.43, 35.96, 36.25, 39.94, 40.12, 41.03, 48.07, 77.24, 108.27, 110.73, 123.90, 127.37, 141.70, 151.84. Anal. Calcd for C$_{27}$H$_{41}$NO$_7$S: C, 61.92; H, 7.89; N, 2.67. Found: C, 62.14; H, 7.98; N, 2.81.

cis-Adamantane-2-spiro-3'-8'-[4'-[2'-(4'-thiomorpholinyl)ethoxy]phenyl]-1',2',4'-trioxaspiro[4.5]decane mesylate (OZ460). Step 1. To a solution of thiomorpholine (2.0 g, 19.4 mmol) and 2-bromoethanol (2.9 g, 23.3 mmol) in acetonitrile (50 ml) was added powdered K$_2$CO$_3$ (13.4 g, 96.9 mmol). After the reaction mixture was refluxed overnight, it was filtered and concentrated. The residue was dissolved in water (50 ml) and extracted with EtOAc (2×25 ml). After the aqueous layer was filtered, water was removed in vacuo. The residue was dissolved in 1,2-dichloroethane (50 ml) before thionyl chloride (5 ml) was added. After the reaction mixture was refluxed for 3 h, the resulting precipitate was filtered, washed with ether (3×25 ml), and dried at 50° C. to afford 4-(2-chloroethyl)thiomorpholine hydrochloride (2.2 g, 87%) as a colorless solid. $^1$H NMR (500 MHz, DMSO-d$_6$) δ 2.78-2.86 (m, 2H), 3.16-3.30 (m, 4H), 3.49 (t, J=6.8 Hz, 2H), 3.70-3.78 (m, 2H), 4.08 (t, J=7.1 Hz, 2H), 11.8 (brs, 1H). Step 2. To a solution of OZ288 (0.50 g, 1.40 mmol) in dry acetonitrile (50 ml) were added powdered NaOH (0.225 g, 5.61 mmol) and tetrabutylammonium hydrogensulfate (0.10 g, 0.28 mmol). After the reaction mixture was stirred at rt for 30 min, 4-(2-chloroethyl)thiomorpholine hydrochloride (0.25 g, 1.26 mmol) was added. The mixture was stirred at 60° C. overnight before the inorganic solid was filtered off and washed with EtOAc (2×25 ml). After removal of the solvents in vacuo, the residue was dissolved in EtOAc (50 ml), washed with water and brine, and dried over MgSO$_4$. Removal of the solvent in vacuo afforded OZ460 free base (0.60 g, 88%) as a colorless solid. To the solution of OZ460 free base (0.60 g, 1.23 mmol) in EtOAc (10 ml) at 0° C. was added dropwise a solution of methanesulfonic acid (0.14 g, 1.4 mmol) in ether (10 ml). The resulting solid was filtered, washed with ether (25 ml), and dried under vacuum at 40° C. to afford trioxolane OZ460 (0.56 g, 78%) as a colorless solid. mp 155-157° C.; $^1$H NMR (500 MHz, CDCl$_3$) δ 1.61-2.08 (m, 22H), 2.46-2.55 (m, 1H), 2.70 (d, J=14.6 Hz, 2H), 2.81 (s, 3H), 3.12-3.24 (m, 2H), 3.44 (t, J=13.3 Hz, 2H), 3.52-3.60 (m, 2H), 3.95 (d, J=12.2 Hz, 2H), 4.42-4.49 (m, 2H), 6.83 (d, J=8.8 Hz, 2H), 7.14 (d, J=8.8 Hz, 2H), 11.42 (s, 1H); $^{13}$C NMR (125.7 MHz, CDCl$_3$) δ 24.98, 26.44, 26.84, 31.55, 34.63, 34.76, 36.37, 36.75, 39.39, 41.98, 54.76, 57.13, 62.58, 108.28, 111.40, 114.42, 127.96, 139.99, 155.33. Anal. Calcd for C$_{29}$H$_{43}$NO$_7$S$_2$: C, 59.87; H, 7.45; N, 2.41. Found: C, 60.03; H, 7.59; N, 2.32.

cis-Adamantane-2-spiro-3'-8'-[4'-[3'-(4'-morpholinyl)propoxy]phenyl]-1',2',4'-trioxaspiro[4.5]decane mesylate (OZ461). Step 1. To a solution of morpholine (1.0 g, 11.47 mmol) and 1-chloro-3-iodopropane (2.35 g, 11.5 mmol) in dry THF (30 ml) was added activated zinc powder (0.75 g, 11.47 mmol). After the mixture was stirred at rt overnight, it was filtered, washed with EtOAc (20 ml), and concentrated. The residue was dissolved in EtOAc (50 ml), washed with 10% aq. NaHCO$_3$ (10 ml), water (2×10 ml), dried over MgSO$_4$, and concentrated. The residue was dissolved in ether (20 ml) before a 1 M ethereal HCl solution (11.5 ml, 11.5 mmol) was added dropwise at 0° C. The resulting precipitate was filtered, washed with ether (2×10 ml), and dried to afford 4-(3-chloropropyl)morpholine hydrochloride (0.70 g, 31%) as a colorless solid. $^1$H NMR (500 MHz, DMSO-d$_6$) δ 2.17-2.28 (m, 2H), 3.01-3.09 (m, 2H), 3.15-3.19 (m, 2H), 3.39-3.42 (m, 2H), 3.76 (t, J=6.4 Hz, 2H), 3.81-3.86 (m, 2H), 3.92-3.96 (m, 2H), 11.46 (brs, 1H). Step 2. To a solution of OZ288 (0.50 g, 1.40 mmol) in dry acetonitrile (50 ml) were added powdered NaOH (0.225 g, 5.61 mmol) and tetrabutylammonium hydrogensulfate (0.1 g, 0.28 mmol). After the reaction mixture was stirred at rt for 30 min, 4-(3-chloropropyl)morpholine hydrochloride (0.25 g, 1.26 mmol) was added. The mixture was stirred at 60° C. overnight before the inorganic solid was filtered off and washed with EtOAc (2×25 ml). After removal of the solvents in vacuo, the residue was dissolved in EtOAc (50 ml). The organic layer was washed with water, brine, dried over MgSO$_4$, and concentrated. After the residue was dissolved in EtOAc (20 ml), a solution of methanesulfonic acid (0.14 g, 1.40 mmol) in ether (10 ml) was added dropwise at 0° C. The resulting precipitate was filtered, washed with ether (25 ml), and dried in vacuo at 40° C. to afford trioxolane OZ461 (0.475 g, 58%) as a colorless solid. mp 158-160° C.; $^1$H NMR (500 MHz, CDCl$_3$) δ 1.61-2.07 (m, 22H), 2.32-2.40 (m, 2H), 2.44-2.55 (m, 1H), 2.79 (s, 3H), 2.88-2.98 (m, 2H), 3.22-3.31 (m, 2H), 3.57 (d, J=12.2 Hz, 2H), 3.97-4.18 (m, 6H), 6.79 (d, J=8.8 Hz, 2H), 7.11 (d, J=8.8 Hz, 2H), 11.39 (brs, 1H); $^{13}$C NMR (125.7 MHz, CDCl$_3$) δ 23.63, 26.41, 26.80, 31.54, 34.63, 34.73, 36.34, 36.72, 39.37, 41.93, 52.23, 55.81, 63.69, 64.51, 108.29, 111.32, 114.20, 127.71, 139.10, 156.40. Anal. Calcd for C$_{30}$H$_{45}$NO$_8$S: C, 62.15; H, 7.82; N, 2.42. Found: C, 62.05; H, 7.63; N, 2.51.

cis-Adamantane-2-spiro-3'-8'-[4'-[3'-(4'-thiomorpholinyl)propoxy]phenyl]-1',2',4'-trioxaspiro[4.5]decane mesylate (OZ462). Step 1. To a solution of thiomorpholine (1.0 g, 9.7 mmol) and 1-chloro-3-iodopropane (1.98 g, 9.7 mmol) in dry THF (30 ml) was added activated zinc powder (0.64 g, 9.7 g atom). After the mixture was stirred at rt overnight, it was filtered, washed with EtOAc (20 ml), and concentrated. The residue was dissolved in EtOAc (50 ml), washed with 10% aq. NaHCO$_3$ (10 ml), water (2×10 ml), dried over MgSO$_4$, and concentrated. The residue was dissolved in ether (20 ml) before a 1 M ethereal HCl solution (9.7 ml, 9.7 mmol) was added dropwise at 0° C. The resulting precipitate was filtered, washed with ether (2×10 ml), and dried to afford 4-(3-chloropropyl)thiomorpholine hydrochloride (0.40 g, 19%) as a colorless solid. $^1$H NMR (500 MHz, DMSO-d$_6$) δ 2.20-2.25 (m, 2H), 2.78-2.81 (m, 2H), 3.09-3.27 (m, 6H), 3.68-3.71 (m, 2H), 3.74 (t, J=6.4 Hz, 2H), 11.20 (brs, 1H). Step 2. To a solution of OZ288 (0.38 g, 1.07 mmol) in dry acetonitrile (50 ml) were added powdered NaOH (0.09 g, 2.13 mmol) and tetrabutylammonium hydrogensulfate (0.07 g, 0.21 mmol). After the mixture was stirred at rt for 30 min, 4-(3-chloropropyl)thiomorpholine hydrochloride (0.23 g, 1.07 mmol) was added. The mixture was stirred at 60° C. overnight before the inorganic solid was filtered off and washed with EtOAc (2×25 ml). After removal of the solvents in vacuo, the residue was dissolved in EtOAc (50 ml). The organic layer was washed with water, brine, dried over MgSO$_4$, and concentrated to afford OZ462 free base (0.433 g, 81%) as a colorless solid. To a solution of the above free base (0.41 g, 0.82 mmol) in EtOAc (10 ml) at 0° C. was added dropwise a solution of methanesulfonic acid (0.08 g, 0.82 mmol) in ether (10 ml). The resulting precipitate was filtered, washed with ether (25 ml), and dried under vacuum at 40° C. to afford trioxolane OZ462 (0.42 g, 86%) as a colorless solid. mp 156-158° C.; $^1$H NMR (500 MHz, CDCl$_3$) δ 1.64-2.08 (m, 22H), 2.32-2.41 (m, 2H), 2.46-2.54 (m, 1H), 2.70 (d, J=14.7 Hz, 2H), 2.80 (s, 3H), 2.96-3.07 (m, 2H), 3.24-3.34 (m, 2H), 3.45-3.54 (m, 2H), 3.87 (d, J=11.8 Hz, 2H), 4.06 (t, J=5.4 Hz, 2H), 6.79 (d, J=8.8 Hz, 2H), 7.12 (d, J=8.3 Hz, 2H), 11.19 (brs, 1H); $^{13}$C NMR (125.7 MHz, CDCl$_3$) δ 23.66, 24.86, 26.44, 26.84, 31.57, 34.66, 34.76, 36.37, 36.75, 39.42, 41.97, 54.35, 56.23, 64.61, 108.32, 111.36, 114.22, 127.74, 139.14, 156.40. Anal. Calcd for C$_{30}$H$_{45}$NO$_7$S$_2$: C, 60.48; H, 7.61; N, 2.35. Found: C, 60.60; H, 7.54; N, 2.17.

cis-Adamantane-2-spiro-3'-8'-[4'-[2'-(1'-oxido-4'-thiomorpholinyl)ethoxy]phenyl]-1',2',4'-trioxaspiro[4.5]decane mesylate (OZ464). Step 1. To a solution of ethanolamine (0.54 g, 8.82 mmol) in water (20 ml) was added divinylsulfoxide (1.0 g, 9.8 mmol). After the reaction mixture was refluxed for 0.5 h, the mixture was concentrated and dried at 50° C. to afford 4-(2-hydroxyethyl)thiomorpholine 1-oxide (1.50 g, 94%) as a colorless liquid. $^1$H NMR (500 MHz, CDCl$_3$) δ 2.65 (t, J=5.4 Hz, 2H), 2.75-3.02 (m, 6H), 3.05-3.31 (m, 3H), 3.66 (t, J=5.4 Hz, 2H). Step 2. To a solution of OZ288 (0.50 g, 1.4 mmol), 4-(2-hydroxyethyl)thiomorpholine 1-oxide (0.34 g, 2.1 mmol), triphenylphosphine (0.55 g, 2.1 mmol), and triethylamine (0.29 ml, 2.1 mmol) in dry THF (50 ml) at 0° C. was added dropwise a solution of DIAD (0.43 g, 2.1 mmol) in THF (10 ml). After stirring at rt overnight, the solvent was removed under vacuum. The residue was dissolved in EtOAc (50 ml), washed with water (3×50 ml), dried over MgSO$_4$, and concentrated. The residue was purified by chromatography (silica gel, 50% EtOH in EtOAc) to afford OZ464 free base (0.51 g, 73%) as a colorless solid. To a solution of OZ464 free base (0.51 g, 1.0 mmol) in EtOAc (10 ml) at 0° C. was added dropwise a solution of methanesulfonic acid (0.14 g, 1.4 mmol) in ether (10 ml). The resulting precipitate was filtered, washed with ether (25 ml), and dried in vacuo at 40° C. to afford trioxolane OZ464 (0.51 g, 85%) as a colorless solid. mp 139-141° C.; $^1$H NMR (500 MHz, DMSO-$d_6$) δ 1.45-1.98 (m, 22H), 2.37 (s, 3H), 2.53-2.64 (m, 1H), 3.08-3.26 (m, 4H), 3.41-3.92 (m, 6H), 4.36 (brs, 2H), 6.95 (J=8.8 Hz, 2H), 7.17 (J=8.3 Hz, 2H), 10.06 (s, 1H); $^{13}$C NMR (125.7 MHz, DMSO-$d_6$) δ 26.00, 26.41, 31.47, 34.26, 34.44, 35.97, 36.27, 39.90, 40.90, 42.09, 42.46, 55.80, 62.12, 108.29, 110.72, 114.89, 127.72, 139.13, 155.99. Anal. Calcd for $C_{29}H_{43}NO_8S_2$: C, 58.27; H, 7.25; N, 2.34. Found: C, 58.46; H, 7.14; N, 2.36.

cis-Adamantane-2-spiro-3'-8'-[4'-[3'-(1'-oxido-4'-morpholinyl)propoxy]phenyl]-1',2',4'-trioxaspiro[4.5]decane mesylate (OZ466). Step 1. To a solution of 3-amino-1-propanol (1.33 g, 17.64 mmol) in water (30 ml) was added divinylsulfoxide (2.0 g, 19.6 mmol). After the reaction mixture was refluxed for 0.5 h, it was concentrated and dried in vacuo at 50° C. to afford 4-(3-hydroxypropyl)thiomorpholine 1-oxide (3.0 g, 96%) as a colorless liquid. $^1$H NMR (500 MHz, CDCl$_3$) δ 1.71-1.85 (m, 2H), 2.65 (t, J=6.4 Hz, 2H), 2.75-2.99 (m, 6H), 3.01-3.27 (m, 2H), 3.73 (t, J=5.9 Hz, 2H), 4.22 (brs, 1H). Step 2. To a solution of OZ288 (0.50 g, 1.4 mmol), 4-(3-hydroxypropyl)thiomorpholine 1-oxide (0.50 g, 2.8 mmol), triphenylphosphine (0.74 g, 2.8 mmol), and triethylamine (0.4 ml, 2.8 mmol) in dry THF (50 ml) at 0° C. was added dropwise a solution of DIAD (0.57 g, 2.8 mmol) in THF (10 ml). After stirring at rt overnight, the solvent was removed in vacuo. The residue was dissolved in EtOAc (50 ml) and washed with water (3×50 ml), dried over MgSO$_4$, and concentrated. The residue was purified by chromatography (silica gel, 50% EtOH in EtOAc) to afford OZ466 free base (0.47 g, 65%) as a colorless solid. To a solution of OZ466 free base (0.47 g, 0.91 mmol) in EtOAc (10 ml) at 0° C. was added dropwise a solution of methanesulfonic acid (0.09 g, 0.91 mmol) in ether (10 ml). The resulting precipitate was filtered, washed with ether (25 ml), and dried in vacuo at 40° C. to afford trioxolane OZ466 (0.50 g, 90%) as a colorless solid. mp 156-158° C.; $^1$H NMR (500 MHz, DMSO-$d_6$) δ 1.45-1.98 (m, 22H), 2.12-2.21 (m, 2H), 2.39 (s, 3H), 2.51-2.61 (m, 1H), 3.04-3.85 (m, 10H), 4.02 (t, J=6.1 Hz, 2H), 6.87 (d, J=8.8 Hz, 2H), 7.13 (d, J=8.8 Hz, 2H), 9.78 (brs, 1H); $^{13}$C NMR (125.7 MHz, DMSO-$d_6$) δ 23.50, 26.01, 26.42, 31.49, 34.29, 34.45, 35.98, 36.28, 40.89, 42.13, 54.50, 64.91, 108.32, 110.73, 114.63, 127.65, 138.48, 156.68. Anal. Calcd for $C_{30}H_{45}NO_8S_2$: C, 58.89; H, 7.41; N, 2.29. Found: C, 57.47; H, 6.94; N, 2.23.

cis-Adamantane-2-spiro-3'-8'-[4'-[3'-[4'-(methylsulfonyl)-1'-piperazinyl]propoxy]phenyl]1',2',4'-trioxaspiro [4.5]decane p-tosylate (OZ482). Step 1. To a suspension of 1-(3-chloropropyl)piperazine dihydrochloride (2.0 g, 8.18 mmol) in CH$_2$Cl$_2$ (50 ml) at 0° C. was added dropwise triethylamine (11.4 ml, 81.8 mmol) followed by a solution of methanesulfonyl chloride (0.8 ml, 9.81 mmol) in CH$_2$Cl$_2$ (10 ml). The reaction mixture was stirred at rt overnight and quenched with water. The organic layer was washed with water (3×25 ml), dried over MgSO$_4$, and filtered. After removal of the solvent under vacuum, the residue was dissolved in ether (50 ml) and ethereal HCl (6.0 ml, 1M in ether, 6.0 mmol) was added dropwise at 0° C. The resulting precipitate was filtered, washed with ether (3×10 ml), and dried at 40° C. to afford 1-(3-chloropropyl)-4-(methanesulfonyl)piperazine hydrochloride (1.35 g, 60%). $^1$H NMR (500 MHz, DMSO-$d_6$) δ 2.18-2.26 (m, 2H), 3.00 (s, 3H), 3.04-3.18 (m, 2H), 3.18-3.23 (m, 2H), 3.32 (t, J=12.2 Hz, 2H), 3.55-3.58 (m, 2H), 3.67-3.69 (m, 2H), 3.76 (t, J=6.4 Hz, 2H), 11.6 (brs, 1H). Step 2. To a solution of OZ288 (0.50 g, 1.4 mmol) in dry acetonitrile (50 ml) were added powdered NaOH (0.225 g, 5.61 mmol) and tetrabutylammonium hydrogensulfate (0.095 g, 0.28 mmol). After the reaction mixture was stirred at rt for 30 min, 1-(3-chloropropyl)-4-(methanesulfonyl)piperazine hydrochloride (0.39 g, 1.4 mmol) was added. The reaction mixture was stirred at 60° C. overnight and cooled to rt. The inorganic solid was filtered off and washed with EtOAc (2×25 ml). After removal of the solvents under vacuum, the residue was dissolved in EtOAc (50 ml). The organic layer was washed with water and brine, dried over MgSO$_4$, filtered, and concentrated. The residue was purified by chromatography (silica gel, 50% EtOH in EtOAc) to afford the free base (0.17 g, 22%) as a colorless solid. To a solution of the above free base (0.17 g, 0.30 mmol) in EtOAc (10 ml) at 0° C. was added dropwise a solution of p-toluenesulfonic acid monohydrate (0.060 g, 0.30 mmol) in ether (10 ml). The resulting precipitate was filtered, washed with ether (25 ml), and dried under vacuum at 40° C. to afford trioxolane OZ482 (0.20 g, 88%) as a colorless solid. mp 148-150° C.; $^1$H NMR (500 MHz, DMSO-$d_6$) δ 1.48-1.59 (m, 2H), 1.62-1.96 (m, 20H), 2.06-2.15 (m, 2H), 2.29 (s, 3H), 2.51-2.59 (m, 1H), 3.02 (s, 3H), 3.05-3.21 (m, 4H), 3.26-3.36 (m, 2H), 3.59-3.78 (m, 4H), 4.01 (t, J=5.8 Hz, 2H), 6.86 (d, J=8.8 Hz, 2H), 7.12 (d, J=7.8 Hz, 2H), 7.13 (d, J=8.3 Hz, 2H), 7.49 (d, J=7.8 Hz, 2H), 9.51 (brs, 1H); $^{13}$C NMR (125.7 MHz, DMSO-$d_6$) δ 20.95, 23.69, 25.98, 26.39, 31.48, 34.26, 34.43, 35.27, 35.96, 36.25, 40.86, 42.70, 50.77, 53.32, 64.82, 108.30, 110.72, 114.59, 125.66, 127.65, 128.27, 137.89, 138.49, 145.72, 156.64. Anal. Calcd for $C_{37}H_{52}N_2O_9S_2$: C, 60.63; H, 7.15; N, 3.82. Found: C, 60.50; H, 7.31; N, 3.40.

cis-Adamantane-2-spiro-3'-8'-[4'-[2'-[4'-(methylsulfonyl)-1'-piperazinyl]ethoxy]phenyl]-1',2',4'-trioxaspiro[4.5] decane mesylate (OZ485). Step 1. To a solution of N-(2-hydroxyethyl)piperazine (2.00 g, 15.36 mmol) in 1,2-dichloroethane (50 ml) at 0° C. was added dropwise a solution of thionyl chloride (5 ml) in 1,2-dichloroethane (5 ml). After the addition, the reaction mixture was refluxed for 4 h and cooled to rt. After the solvent was removed under vacuum, the residue was triturated with ether (50 ml). The resulting precipitate was filtered, washed with ether (3×25 ml), and dried at 50° C. to afford N-(2-chloroethyl)piperazine dihydrochloride (3.20 g, 95%) as a colorless solid. Step 2. To a solution of N-(2-chloroethyl)piperazine dihydrochloride (1.00 g, 4.54 mmol) and triethylamine (6.3 ml, 45.5 mmol) in 1,2-dichloroethane (25 ml) at 0° C. was added dropwise a solution of methanesulfonyl chloride (1.04 g, 9.08 mmol) in 1,2-dichloroethane (10 ml). After the reaction mixture was stirred at rt overnight, it was quenched with water (25 ml). The organic layer was washed with water (3×25 ml) and dried over MgSO$_4$. Removal of the solvent under vacuum furnished 1-(2-chloroethyl)-4-(methanesulfonyl)piperazine (0.87 g, 85%) as a viscous oil. $^1$H NMR (500 MHz, CDCl$_3$) δ 2.63-2.65 (m, 4H), 2.77-2.8 (m, 5H), 3.27 (t, J=4.9 Hz, 4H), 3.59 (t, J=6.8 Hz, 2H). Step 3. To a solution of OZ288 (0.50 g, 1.40 mmol) in dry acetonitrile (50 ml) were added powdered NaOH (0.17 g, 4.21 mmol) and tetrabutylammonium hydrogensulfate (0.10 g, 0.28 mmol). After the reaction mixture was stirred at rt for 30 min, a solution of 1-(2-chloroethyl)-4-(methanesulfonyl)piperazine (0.48 g, 2.10 mmol) in acetonitrile (5 ml) was added. After the reaction mixture was stirred at 60° C. overnight and cooled to rt, the inorganic solid was filtered off and washed with EtOAc (2×25 ml). After the filtrate was concentrated, the residue was dissolved in EtOAc (50 ml). The organic layer was washed with water and brine and dried over MgSO$_4$. After removal of the solvent, the residue was purified by chromatography (silica gel, 50% EtOH in EtOAc) to afford the free base (0.49 g, 64%) as a colorless solid. $^1$H NMR (500 MHz, CDCl$_3$) δ 1.62-2.04 (m, 22H), 2.46-2.54 (m, 1H), 2.69 (t, J=4.9 Hz, 4H), 2.77 (s, 3H), 2.84 (t, J=5.4 Hz, 2H), 3.26 (t, J=4.9 Hz, 4H), 4.07 (t, J=5.4 Hz, 2H), 6.82 (d, J=8.8 Hz, 2H), 7.11 (d, J=8.3 Hz, 2H). To a solution of the above free base (0.49 g, 0.9 mmol) in EtOAc (10 ml) at 0° C. was added dropwise a solution of methanesulfonic acid (0.08 g, 0.81 mmol) in ether (10 ml). The resulting precipitate was filtered, washed with ether (3×10 ml), and dried under vacuum at 40° C. to afford trioxolane OZ485 (0.52 g, 90%) as a colorless solid. mp 140-142° C.; $^1$H NMR (500 MHz, DMSO-d$_6$) δ 1.48-1.59 (m, 2H), 1.61-1.96 (m, 20H), 2.37 (s, 3H), 2.52-2.62 (m, 1H), 3.02 (s, 3H), 3.11-3.34 (m, 4H), 3.57-3.79 (m, 6H), 4.33 (brs, 2H), 6.95 (d, J=7.8 Hz, 2H), 7.17 (d, J=7.8 Hz, 2H), 9.95 (brs, 1H); $^{13}$C NMR (125.7 MHz, DMSO-d$_6$) δ 25.99, 26.40, 31.47, 34.26, 34.44, 35.26, 35.97, 36.26, 39.94, 40.89, 42.52, 51.21, 54.73, 62.24, 108.30, 110.74, 114.89, 127.74, 139.14, 155.99. Anal. Calcd for C$_{30}$H$_{46}$N$_2$O$_9$S$_2$·0.3H$_2$O: C, 56.05; H, 7.21; N, 4.36. Found: C, 55.48; H, 7.25; N, 4.04.

cis-Adamantane-2-spiro-3'-8'-[4'-(cis-4'-aminocyclohexyloxy)phenyl]-1',2',4'-trioxaspiro[4.5]decane mesylate (OZ493). Step 1. Diisopropyl azodicarboxylate (0.69 ml, 3.51 mmol) was added dropwise to a mixture of OZ288 (1.00 g, 2.81 mmol), N-(trans-4-hydroxycyclohexyl)phthalimide (0.85 g, 3.47 mmol), and triphenylphosphine (0.92 g, 3.51 mmol) in THF (50 ml) at 0° C. under N$_2$. The resulting mixture was stirred at rt for 24 h. After removal of the solvent, the crude product was purified by crystallization from EtOH to afford the desired phenol ether (0.95 g, 58%) as a colorless solid. mp 145-146° C.; $^1$H NMR (500 MHz, CDCl$_3$) δ 1.51-2.08 (m, 26H), 2.16-2.25 (m, 2H), 2.44-2.54 (m, 1H), 2.66-2.78 (m, 2H), 4.15-4.24 (m, 1H), 4.53-4.58 (m, 1H), 6.90-6.96 (m, 2H), 7.09-7.15 (m, 2H), 7.67-7.73 (m, 2H), 7.79-7.86 (m, 2H); $^{13}$C NMR (125.7 MHz, CDCl$_3$) δ 23.95, 26.50, 26.89, 29.27, 31.65, 34.77, 34.81, 36.41, 36.82, 42.10, 50.17, 69.55, 108.48, 111.34, 116.26, 123.03, 127.61, 132.07, 133.79, 138.40, 155.60, 168.33. Step 2. A mixture of the above phenol ether (1.45 g, 2.49 mmol) and hydrazine monohydrate (2 ml) in chloroform (40 ml) and methanol (6 ml) was heated at 50° C. for 24 h. After the reaction mixture was cooled to rt, filtered to remove the solid by-product, the filtrate was washed with water (2×20 ml) and brine (20 ml), and dried over MgSO$_4$, filtered, and concentrated. The residue was dissolved in CH$_2$Cl$_2$ (5 ml) and then a solution of methanesulfonic acid (0.23 g, 2.4 mmol) in ethyl acetate (20 ml) was added. The precipitate was collected by filtration to afford trioxolane OZ493 (1.11 g, 81%) as a colorless solid. mp 158-159° C.; $^1$H NMR (500 MHz, DMSO-d$_6$) δ 1.48-1.96 (m, 30H), 2.32 (s, 3H), 2.51-2.60 (m, 1H), 3.04-3.17 (m, 1H), 4.52 (s, 1H), 6.86 (d, J=8.3 Hz, 2H), 7.12 (d, J=8.3 Hz, 2H), 7.78 (brs, 3H); $^{13}$C NMR (125.7 MHz, DMSO-d$_6$) δ 24.93, 25.98, 26.39, 27.14, 31.46, 34.28, 34.43, 35.95, 36.25, 40.88, 48.51, 69.73, 108.30, 110.71, 116.11, 127.72, 138.32, 155.31. Anal. Calcd for C$_{29}$H$_{43}$NO$_7$S: C, 63.36; H, 7.88; N, 2.55. Found: C, 64.26; H, 7.88; N, 2.26.

cis-Adamantane-2-spiro-3'-8'-(4'-oxocyclohexyl)-1',2',4'-trioxaspiro[4.5]decane (OZ495). A solution of O-methyl 2-adamantanone oxime (2.00 g, 11.2 mmol) and 4,4'-bicyclohexanone (4.34 g, 22.4 mmol) in cyclohexane (150 ml) and CH$_2$Cl$_2$ (75 ml) was treated with ozone according to the general procedure. After removal of the solvents, the crude product was purified by crystallization from EtOH/H$_2$O (10:3) to afford trioxolane OZ495 (2.50 g, 63%) as a colorless solid. mp 90-91° C.; $^1$H NMR (500 MHz, CDCl$_3$) δ 1.05-2.11 (m, 28H), 2.21-2.49 (m, 4H); $^{13}$C NMR (125.7 MHz, CDCl$_3$) δ 26.47, 26.87, 27.28, 29.87, 34.39, 34.79, 36.39, 36.79, 40.42, 40.84, 41.02, 108.68, 111.34, 212.17. Anal. Calcd for C$_{22}$H$_{32}$O$_4$: C, 73.30; H, 8.95. Found: C, 73.80; H, 8.92.

cis-Adamantane-2-spiro-3'-8'-[4'-(5'-aminopentoxy)phenyl]-1',2',4'-trioxaspiro[4.5]decane mesylate (OZ498). Step 1. A mixture of phthalic anhydride (1.48 g, 10 mmol) and 5-amino-1-pentanol (1.03 g, 10 mmol) in toluene (20 ml) was heated under reflux overnight. The solvent was removed under vacuum, and the residue was purified by chromatography to afford N-(5-hydroxypentyl)phthalimide (2.00 g, 88%) as a colorless oil. $^1$H NMR (500 MHz, CDCl$_3$) δ 1.37-1.48 (m, 2H), 1.56-1.67 (m, 2H), 1.67-1.79 (m, 2H), 3.64 (t, J=6.5 Hz, 2H), 3.70 (t, J=7.5 Hz, 2H), 7.66-7.76 (m, 2H), 7.80-7.99 (m, 2H). Step 2. Diisopropyl azodicarboxylate (0.69 ml, 3.51 mmol) was added dropwise to a mixture of OZ288 (0.50 g, 1.4 mmol), N-(5-hydroxypentyl)phthalimide (0.65 g, 2.79 mmol), triphenylphosphine (0.92 g, 3.51 mmol), and triethylamine (0.5 ml, 3.51 mmol) in THF (50 ml) at 0° C. under N$_2$ atmosphere. The resulting mixture was stirred at rt for 24 h. After removal of the solvent, the crude product was purified by crystallization from EtOH to afford the desired phenol ether (0.35 g, 44%) as a colorless solid. mp 115-116° C.; $^1$H NMR (500 MHz, CDCl$_3$) δ 1.46-2.08 (m, 28H), 2.43-2.53 (m, 1H), 3.71 (t, J=7.0 Hz, 2H), 3.92 (t, J=6.5 Hz, 2H), 6.79 (d, J=9.0 Hz, 2H), 7.09 (d, J=9.0 Hz, 2H), 7.67-7.75 (m, 2H), 7.80-7.99 (m, 2H); $^{13}$C NMR (125.7 MHz, CDCl$_3$) δ 23.42, 26.49, 26.89, 28.33, 28.85, 31.65, 34.76, 34.81, 36.41, 36.81, 37.85, 42.05, 67.55, 108.46, 111.34, 114.34, 123.18, 127.56, 132.15, 133.86, 138.20, 157.34, 168.43. Step 3. A mixture of the above phenol ether (0.30 g, 0.53 mmol) and hydrazine monohydrate (1 ml) in chloroform (30 ml) and methanol (3 ml) was heated at 50° C. for 24 h. After the reaction mixture was cooled to rt and filtered to the remove a solid by-product, the filtrate was washed with water (2×10 ml) and brine (10 ml), dried over MgSO$_4$, filtered, and concentrated. The residue was dissolved in CH$_2$Cl$_2$ (5 ml) and a solution of methanesulfonic acid (0.05 g, 0.52 mmol) in ethyl acetate (20 ml) was added. The precipitate was collected by filtration to afford trioxolane OZ498 (0.19 g, 68%) as a colorless solid. mp 155-156° C.; $^1$H NMR (500 MHz, DMSO-d$_6$) δ 1.38-1.98 (m, 28H), 2.30 (brs, 3H), 2.50-2.59 (m, 1H), 2.76-2.85 (m, 2H), 3.92 (t, J=6.3 Hz, 2H), 6.83 (d, J=8.8 Hz, 2H), 7.11 (d, = 8.3 Hz, 2H), 7.63 (brs, 3H); $^{13}$C NMR (125.7 MHz, DMSO-d$_6$) δ 22.72, 25.98, 26.39, 26.90, 28.35, 31.49, 34.28, 34.44, 35.96, 36.25, 38.97, 40.86, 67.22, 108.32, 110.71, 114.44, 127.58, 138.04, 157.08. Anal. Calcd for C$_{28}$H$_{43}$NO$_7$S: C, 62.54; H, 8.06; N, 2.60. Found: C, 62.55; H, 7.93; N, 2.76.

cis-Adamantane-2-spiro-3'-8'-[4'-(4'-morpholinyl)cyclohexyl]-1',2',4'-trioxaspiro[4.5]decane mesylate (OZ499). To a solution of OZ495 (0.23 g, 0.64 mmol) in CH$_2$Cl$_2$ (10 ml) and ClCH$_2$CH$_2$Cl (10 ml) were added morpholine (1.0 ml, mmol) and acetic acid (2.5 ml). The resulting mixture was stirred at rt for 2 h before sodium triacetoxyborohydride (0.22 g, 1.03 mmol) was added. The reaction mixture was stirred overnight and then quenched with 1 M aq. NaOH (2 ml). The organic layer was separated and washed with water (10 ml) and brine (10 ml), dried over MgSO$_4$, and concentrated. The residue was dissolved in CH$_2$Cl$_2$ (5 ml) and a solution of methanesulfonic acid (0.06 g, 0.63 mmol) in ethyl acetate (20 ml) was added. The precipitate was collected by filtration to afford trioxolane OZ499 (0.11 g, 32%) as a colorless solid. mp 150-152° C.; $^1$H NMR (500 MHz, CDCl$_3$) δ 1.02-1.51 (m, 6H), 1.61-2.08 (m, 26H), 2.82 (s, 3H), 2.83-2.94 (m, 2H), 2.99-3.09 (m, 1H), 3.49 (d, J=11.2 Hz, 2H), 4.00 (dd, J=13.2, 2.9 Hz, 2H), 4.23 (t, J=12.0 Hz, 2H), 11.05 (brs, 1H); $^{13}$C NMR (125.7 MHz, CDCl$_3$) δ 21.87, 26.15, 26.49, 26.87, 27.98, 33.41, 33.99, 34.78, 36.40, 36.51, 36.80, 39.58, 48.99, 63.82, 66.51, 108.59, 111.34. Anal. Calcd for $C_{27}H_{45}NO_7S$: C, 61.45; H, 8.60; N, 2.65. Found: C, 61.53; H, 8.44; N, 2.57.

cis-Adamantane-2-spiro-3'-8'-[4'-[3'-[(2'-hydroxy-2'-methylpropyl)amino]propoxy]phenyl]-1',2',4'-trioxaspiro[4.5]decane p-tosylate (OZ505). A solution of 1,2-epoxy-2-methylpropane (1 ml, 11 mmol) and the free base of OZ401 (620 mg, 1.5 mmol) in ethanol (10 ml) under Ar was stirred at rt for 2 d and then evaporated to dryness. The residue was dissolved in DCM (30 ml), washed with water (5×30 ml), dried over $MgSO_4$, and evaporated to dryness. The crude product was dissolved in DCM (10 ml), cooled in ice-water bath, and treated with a solution of p-toluenesulfonic acid monohydrate (250 mg, 1.3 mmol) in ethyl ether (30 ml). The resulting precipitate was collected through filtration, washed with ether, and air dried to give trioxolane OZ505 (660 mg, 67%) as a yellowish solid. mp 160-162° C.; $^1$H NMR (500 MHz, DMSO-$d_6$) δ 1.20 (s, 6H), 1.45-1.61 (m, 2H), 1.62-1.98 (m, 20H), 2.04-2.13 (m, 2H), 2.29 (s, 3H), 2.50-2.63 (m, 1H), 2.89-2.95 (m, 2H), 3.02-3.12 (m, 2H), 4.02 (t, J=5.9 Hz, 2H), 5.17 (s, 1H), 6.85 (d, J=8.8 Hz, 2H), 7.11 (d, J=8.3 Hz, 2H), 7.13 (d, J=9.3 Hz, 2H), 7.48 (d, J=7.8 Hz, 2H), 8.20 (brs, 2H); $^{13}$C NMR (125.7 MHz, DMSO-$d_6$) δ 20.95, 25.13, 25.99, 26.39, 27.54, 31.49, 34.27, 34.44, 35.96, 36.26, 40.86, 45.95, 57.15, 64.98, 67.25, 108.31, 110.72, 114.54, 125.66, 127.64, 128.21, 137.75, 138.41, 145.93, 156.67. Anal. Calcd for $C_{36}H_{51}NO_8S$: C, 65.73; H, 7.81; N, 2.13. Found: C, 65.60; H, 7.63; N, 2.30.

cis-Adamantane-2-spiro-3'-8'-(4'-hydroxycyclohexyl)-1',2',4'-trioxaspiro[4.5]decane (OZ508). A solution of $NaBH_4$ (42 mg, 1.1 mmol) in ethanol (10 ml) containing 3 drops of 1.0 M aq NaOH was added to a solution of OZ495 (0.36 g, 1.0 mmol) in THF (5 ml) at 0° C. over a period of 5 min. The reaction was stirred at rt for 1 h before being quenched with EtOAc (10 ml). After removal of the solvents, the residue was dissolved in EtOAc (50 ml) and washed with saturated aq. $NaHCO_3$ (10 ml), water (10 ml), and brine (10 ml). The organic layer was dried over $MgSO_4$, filtered, and concentrated to afford trioxolane OZ508 (0.30 g, 83%, 10:1 mixture of two diastereomers) as a colorless solid. mp 138-140° C.; $^1$H NMR (500 MHz, CDCl$_3$) δ 0.98-2.05 (m, 33H), 3.48-3.55 (m, 1H); $^{13}$C NMR (125.7 MHz, CDCl$_3$) δ 26.48, 26.88, 27.21, 28.15, 34.52, 34.79, 35.77, 36.38, 36.81, 41.18, 41.35, 71.08, 108.94, 111.18. Anal. Calcd for $C_{22}H_{34}O_4$: C, 72.89; H, 9.45. Found: C, 73.02; H, 9.22.

cis-Adamantane-2-spiro-3'-8'-[4'-[2'-(4'-hydroxy-1'-piperidinyl)ethoxy]phenyl]-1',2',4'-trioxaspiro[4.5]decane (OZ513). A mixture of cis-adamantane-2-spiro-3'-8'-[4'-(2'-bromoethoxy)phenyl]-1',2',4'-trioxaspiro[4.5]decane (0.50 g, 1.08 mmol), 4-hydroxypiperidine (0.25 g, 2.5 mmol), and $K_2CO_3$ (2.0 g) in dry acetonitrile (80 ml) was heated at 60° C. for 2 d. After the reaction mixture was cooled to rt and filtered to remove the solid material, the filtrate was concentrated. The residue was washed with water (50 ml) and dried in vacuo to afford trioxolane OZ513 (0.46 g, 88%) as a colorless solid. mp 89-90° C.; $^1$H NMR (500 MHz, CDCl$_3$) δ 1.59-2.09 (m, 27H), 2.25-2.35 (m, 2H), 2.44-2.56 (m, 1H), 2.79 (t, J=6.1 Hz, 2H), 2.81-2.89 (m, 2H), 3.65-3.77 (m, 1H), 4.07 (t, J=5.8 Hz, 2H), 6.83 (d, J=8.8 Hz, 2H), 7.11 (d, J=8.8 Hz, 2H); $^{13}$C NMR (125.7 MHz, CDCl$_3$) δ 26.49, 26.89, 31.65, 34.47, 34.75, 34.81, 36.41, 36.82, 42.06, 51.52, 57.10, 66.08, 108.44, 111.37, 114.46, 127.61, 138.49, 157.10. Anal. Calcd for $C_{29}H_{41}NO_5$: C, 72.02; H, 8.54; N, 2.90. Found: C, 69.37; H, 8.06; N, 2.58.

cis-Adamantane-2-spiro-3'-8'-[[4'-[2'-(4'-morpholinyl)ethoxy]phenyl]methyl]-1',2',4'-trioxaspiro[4.5]decane p-tosylate (OZ527). A mixture of OZ514 (780 mg, 1.81 mmol), NaOH (504 mg, 12.6 mmol), and $Bu_4NHSO_4$ (150 mg, 0.42 mmol) in MeCN (65 ml) was stirred at rt for 30 min before N-(2-chloroethyl)morpholine hydrochloride (1.18 g, 6.3 mmol) was added. The resulting solution was stirred at 60° C. for 16 h, quenched with ice-water (75 ml), and extracted with DCM (6×30 ml). The DCM layers were combined, washed with 10% aq. EtOH (2×30 ml), dried over $Na_2SO_4$, and evaporated to dryness. The residue was crystallized from MeOH to yield the desired free base (510 mg, 58%) as needles. mp 105-106° C.; $^1$H NMR (500 MHz, CDCl$_3$) δ 1.17-1.26 (m, 2H), 1.45-1.98 (m, 21H), 2.44 (d, J=6.8 Hz, 2H), 2.58 (t, J=4.4 Hz, 4H), 2.79 (t, J=5.9 Hz, 2H), 3.73 (t, J=4.6 Hz, 4H), 4.09 (d, J=5.8 Hz, 2H) 6.82 (d, J=8.3 Hz, 2H), 7.03 (d, J=8.3 Hz, 2H); $^{13}$C NMR (125.7 MHz, CDCl$_3$) δ 26.5, 26.9, 29.9, 34.2, 34.775, 34.782, 36.4, 36.8, 38.3, 41.9, 54.1, 57.7, 65.7, 66.9, 109.0, 111.2, 114.3, 125.9, 130.0, 133.2, 156.9. A mixture of the above free base (310 mg, 0.64 mmol) and p-toluenesulfonic acid monohydrate (123 mg, 0.64 mmol) in DCM (10 ml) and ether (10 ml) was stirred at rt overnight. The precipitate was collected by filtration, washed with ether (10 ml), and dried under vacuum to afford trioxolane OZ527 (350 mg, 83%) as a colorless solid. mp 146-147° C.; $^1$H NMR (500 MHz, CDCl$_3$) δ 1.16-1.31 (m, 2H), 1.42-2.06 (m, 21H), 2.38 (s, 3H), 2.46 (d, J=6.8 Hz, 2H), 3.02-3.16 (m, 2H), 3.52-3.62 (m, 2H), 3.70 (d, J=12.2 Hz, 2H), 3.92-4.03 (m, 2H), 4.10 (t, J=12.0 Hz, 2H), 4.39-4.49 (m, 2H), 6.75 (d, J=8.3 Hz, 2H), 7.04 (d, J=8.3 Hz, 2H), 7.21 (d, J=7.8 Hz, 2H), 7.79 (d, J=8.3 Hz, 2H), 11.73 (brs, 1H); $^{13}$C NMR (125.7 MHz, CDCl$_3$) δ 21.35, 26.46, 26.85, 29.80, 34.11, 34.77, 36.36, 36.78, 38.20, 41.88, 53.04, 56.97, 62.89, 63.85, 108.90, 111.24, 114.21, 125.88, 128.93, 130.25, 134.50, 140.38, 141.78, 155.21. Anal. Calcd for $C_{36}H_{49}NO_8S$: C, 65.93; H, 7.53; N, 2.14. Found: C, 65.76; H, 7.38; N, 2.13.

cis-Adamantane-2-spiro-3'-8'-[4'-[3'-(4'-formyl-1'-piperazinyl)propoxy]phenyl]-1',2',4'-trioxaspiro[4.5]decane mesylate (OZ534). To a stirred mixture of cis-adamantane-2-spiro-3'-8'-[4'-(3'-bromopropoxy)phenyl]-1',2',4'-trioxaspiro[4.5]decane (0.60 g, 1.26 mmol) and potassium carbonate (2.00 g) in acetonitrile (50 ml) at rt was added 1-piperazinecarboxaldehyde (0.29 g, 2.52 mmol). The reaction mixture was stirred for 48 h at 60° C. and cooled to rt. The inorganic solid was filtered off and washed with EtOAc (2×25 ml). The combined filtrate was evaporated to dryness under vacuum. The residue was dissolved in EtOAc (50 ml), washed with water (3×25 ml), dried over $MgSO_4$, and filtered. Removal of the solvent gave the desired free base as a colorless solid. To a solution of the above free base in EtOAc (10 ml) at 0° C. was added dropwise a solution of methanesulfonic acid (0.12 g, 1.26 mmol) in ether (10 ml). The resulting precipitate was filtered, washed with ether (3×10 ml), and dried under vacuum at 40° C. to afford trioxolane OZ534 (0.65 g, 85%) as a colorless solid. mp 156-158° C.; $^1$H NMR (500 MHz, DMSO-$d_6$) δ 1.45-1.59 (m, 2H), 1.61-1.96 (m, 20H), 2.08-2.17 (m, 2H), 2.34 (s, 3H), 2.48-2.60 (m, 1H), 2.91-3.09 (m, 3H), 3.24-3.33 (m, 2H), 3.34-3.44 (m, 1H), 3.51-3.64 (m, 2H), 3.96 (d, J=14.1 Hz, 1H), 4.02 (t, J=6.1 Hz, 2H), 4.28 (d, J=12.2 Hz, 1H), 6.86 (d, J=8.8 Hz, 2H), 7.14 (d, J=8.8 Hz, 2H), 8.08 (s, 1H), 9.70 (brs, 1H); $^{13}$C NMR (125.7 MHz, DMSO-$d_6$) δ 23.63, 26.00, 26.40, 31.48, 34.27, 34.44, 35.97, 36.13, 36.27, 39.93, 40.87, 41.64, 50.68, 51.51, 53.63, 64.86, 108.31, 110.72, 114.60, 127.65, 138.48, 156.67, 161.30. Anal. Calcd for $C_{31}H_{46}N_2O_8S$: C, 61.36; H, 7.64; N, 4.62. Found: C, 59.91; H, 7.43; N, 3.76.

cis-Adamantane-2-spiro-3'-8'-[4'-[3'-[(trans-4'-hydroxycyclohexyl)amino]propoxy]phenyl]-1',2',4'-trioxaspiro[4.5]decane p-tosylate (OZ535). To a stirred mixture of cis-adamantane-2-spiro-3'-8'-[4'-(3'-bromopropoxy)phenyl]-1',2', 4'-trioxaspiro[4.5]decane (0.60 g, 1.26 mmol) and potassium carbonate (2.00 g) in acetonitrile (50 ml) at rt was added trans-4-aminocyclohexanol (0.29 g, 2.52 mmol). The reaction mixture was stirred for 48 h at 60° C. and cooled to rt. The inorganic solid was filtered off and washed with EtOAc (2×25 ml). The combined filtrate was evaporated to dryness under vacuum. The residue was dissolved in EtOAc (50 ml), washed with water (3×25 ml), dried over $MgSO_4$, and filtered. Removal of the solvent gave the desire free base as a colorless solid. To a solution of the above free base in EtOAc (10 ml) at 0° C. was added dropwise a solution of p-toluenesulfonic acid monohydrate (0.24 g, 1.26 mmol) in ether (10 ml). The resulting precipitate was filtered, washed with ether (3×10 ml), and dried under vacuum at 40° C. to afford trioxolane OZ535 (0.79 g, 92%) as a colorless solid. mp 138-140° C.; $^1$H NMR (500 MHz, DMSO-$d_6$) δ 1.11-1.23 (m, 2H), 1.24-1.38 (m, 2H), 1.45-1.59 (m, 2H), 1.61-1.96 (m, 27H), 2.29 (s, 3H), 2.47-2.60 (m, 1H), 2.91-3.12 (m, 3H), 4.01 (brs, 2H), 4.70 (brs, 1H), 6.85 (d, J=8.3 Hz, 2H), 7.12 (d, J=6.8 Hz, 2H), 7.13 (d, J=6.8 Hz, 2H), 7.49 (d, J=7.8 Hz, 2H), 8.32 (brs, 2H); $^{13}$C NMR (125.7 MHz, DMSO-$d_6$) δ 20.99, 25.93, 26.03, 26.44, 26.87, 31.53, 33.06, 34.31, 34.47, 36.00, 36.29, 40.91, 41.84, 55.48, 64.70, 67.82, 108.34, 110.75, 114.58, 125.68, 127.66, 128.37, 138.13, 138.40, 145.48, 156.73. Anal. Calcd for $C_{38}H_{53}NO_8S$: C, 66.74; H, 7.81; N, 2.05. Found: C, 66.67; H, 7.92; N, 2.07.

cis-Adamantane-2-spiro-3'-8'-[4'-(trans-4'-aminocyclohexyloxy)phenyl]-1',2',4'-trioxaspiro[4.5]decane mesylate (OZ537). Step 1. To a stirred solution of cis-4-aminocyclohexanol hydrochloride (1.0 g, 6.6 mmol) and triethylamine (2 ml) in $CH_2Cl_2$ (25 ml) was added $Boc_2O$ (1.44 g, 6.6 mmol). The resulting mixture was stirred at rt for 3 h. After removal of the solvent, the residue was washed with water (30 ml) and dried in vacuo to give tert-butyl cis-4-hydroxycyclohexylcarbamate (0.80 g, 56%) as a colorless solid. mp 85-86° C.; $^1$H NMR (500 MHz, CDCl$_3$) δ 1.30-1.74 (m, 8H), 1.45 (s, 9H), 3.48-3.60 (m, 1H), 3.86-3.94 (m, 1H), 4.46-4.60 (m, 1H). Step 2. Diisopropyl azodicarboxylate (0.32 ml, 1.68 mmol) was added dropwise to a mixture of OZ288 (0.5 g, 1.4 mmol), tert-butyl cis-4-hydroxycyclohexylcarbamate (0.3 g, 1.4 mmol), and triphenylphosphine (0.44 g, 1.68 mmol) in THF (50 ml) at 0° C. under $N_2$ atmosphere. The resulting mixture was stirred at rt for 24 h. After removal of the solvent, the crude product was purified by crystallization from EtOH to afford the desired phenol ether (0.60 g, 77%) as a colorless solid. mp 150-151° C.; $^1$H NMR (500 MHz, CDCl$_3$) δ 1.18-1.30 (m, 2H), 1.45 (s, 9H), 1.48-2.16 (m, 30H), 2.43-2.54 (m, 1H), 3.45-3.58 (m, 1H), 4.07-4.17 (m, 1H), 4.34-4.48 (m, 1H), 6.80 (d, J=9.0 Hz, 2H), 7.09 (d, J=9.0 Hz, 2H); $^{13}$C NMR (125.7 MHz, CDCl$_3$) δ 26.47, 26.87, 28.40, 30.27, 30.86, 31.62, 34.74, 34.79, 36.39, 36.79, 42.05, 48.76, 75.07, 108.44, 111.36, 115.90, 127.64, 138.54, 155.94, 162.77. Step 3. A mixture of the above phenol ether (0.50 g, 0.90 mmol) and 1.5 M MsOH in THF (6 ml) was stirred at rt for 6 h. The resulting precipitate was filtered off, washed with ether (30 ml), and dried in vacuo to afford trioxolane OZ537 (0.48 g, 96%) as a colorless solid. mp 167-168° C.; $^1$H NMR (500 MHz, DMSO-$d_6$) δ 1.35-1.59 (m, 6H), 1.61-1.96 (m, 22H), 2.02-2.15 (m, 2H), 2.31 (s, 3H), 2.47-2.60 (m, 1H), 3.01-3.15 (m, 1H), 4.17-4.27 (m, 1H), 6.86 (d, J=8.8 Hz, 2H), 7.10 (d, J=8.8 Hz, 2H), 7.78 (brs, 3H); $^{13}$C NMR (125.7 MHz, DMSO-$d_6$) δ 25.99, 26.40, 28.16, 29.31, 31.49, 34.29, 34.45, 35.96, 36.27, 40.88, 48.57, 73.81, 108.34, 110.73, 115.85, 127.70, 138.27, 155.60. Anal. Calcd for $C_{29}H_{43}NO_7S$: C, 63.36; H, 7.88; N, 2.55. Found: C, 63.76; H, 7.78; N, 2.31.

cis-Adamantane-2-spiro-3'-8'-[4'-(3'-amino-3'-methylbutoxy)phenyl]-1',2',4'-trioxaspiro[4.5]decane p-tosylate (OZ539). Step 1. To a solution of $H_2SO_4$ (60 ml, 98%, 1.10 mol) at −5° C. was added dropwise MeCN (25 ml, 0.48 mol) followed by 3-methyl-1,3-butanediol (48 ml, 0.40 mol). The resulting solution was stirred at 0° C. for 1 h, then poured onto ice (300 ml), and washed with ether (2×50 ml). The water layer was alkalized with 15 M aq. NaOH (150 ml) to pH=12 and extracted with ether (3×150 ml). The ether layers were combined, washed with saturated NaCl (2×50 ml), dried over $K_2CO_3$, and evaporated to dryness to yield 2,4,4-trimethyl-5,6-dihydro-1,3 (4H)-oxazine (46.5 g, 91.4%) as a colorless oil (unstable). $^1$H NMR (500 MHz, CDCl$_3$) δ 1.18 (s, 6H), 1.69 (t, J=5.9 Hz, 2H), 1.86 (s, 3H), 4.11 (t, J=5.9 Hz, 2H); $^{13}$C NMR (125.7 MHz, CDCl$_3$) δ 21.0, 29.7, 33.1, 47.2, 61.0, 154.8. Step 2. 2,4,4-trimethyl-5,6-dihydro-1,3 (4H)-oxazine (46.0 g, 0.362 mol) was added dropwise to 6 M aq. NaOH (150 ml) at rt. The resulting mixture was stirred at 80° C. for 20 h, then cooled to rt, and extracted with DCM (3×100 ml). The DCM layers were combined, washed with brine (3×100 ml), dried over $MgSO_4$, and evaporated to yield 3-amino-3-methyl-1-butanol (11.0 g, 29%) as a brown oil. [Note, the brine solution was extracted with DCM (5×100 ml) to recover 3-amino-3-methyl-1-butanol (10.0 g, 27%)]. $^1$H NMR (500 MHz, CDCl$_3$) δ 1.20 (s, 6H), 1.59 (t, J=5.6 Hz, 2H), 2.81 (brs, 3H), 3.83 (t, J=5.6 Hz, 2H); $^{13}$C NMR (125.7 MHz, CDCl$_3$) δ 30.9, 42.6, 50.6, 60.2. Step 3. To a solution of 3-amino-3-methyl-1-butanol (7.20 g, 70 mmol) and Et$_3$N (8 ml) in DCM (40 ml) at 0° C. was added dropwise a solution of Boc$_2$O (15.2 g, 70 mmol) in DCM (20 ml). The resulting mixture was stirred at rt for 2 d, extracted with water (3×20 ml), dried over $Na_2SO_4$, and concentrated. The residue was purified by flash chromatography (silica gel, 0-50% EtOAc in hexane) to yield 3-(tert-butoxycarbonylamino)-3-methyl-1-butanol (2.20 g, 15%) as a colorless oil. $^1$H NMR (500 MHz, CDCl$_3$) δ 1.32 (s, 6H), 1.43 (s, 9H), 1.87 (t, J=6.3 Hz, 2H), 2.33 (brs, 1H), 3.76 (t, J=6.3 Hz, 2H), 4.98 (brs, 1H); $^{13}$C NMR (125.7 MHz, CDCl$_3$) δ 27.7, 28.4, 43.2, 51.8, 59.3, 78.9 (br), 155.0 (br). Step 4. To a solution of OZ288 (890 mg, 2.50 mmol), triphenylphosphine (986 mg, 3.75 mmol), 3-(tert-butoxycarbonylamino)-3-methyl-1-butano (761 mg, 3.75 mmol), and Et$_3$N (0.83 ml, 6.00 mmol) in DCM (30 ml) at 0° C. was added dropwise diisopropyl azodicarboxylate (0.80 ml, 3.75 mmol) in DCM (10 ml). The resulting mixture was stirred overnight, then washed with water (3×20 ml), and concentrated. The residue was purified by flash chromatography (silica gel, 0-9% ether in hexane) to yield the phenol ether (0.77 g, 57%) as a white semi-solid. $^1$H NMR (500 MHz, CDCl$_3$) δ 1.35 (s, 6H), 1.43 (s, 9H), 1.66-2.04 (m, 22H), 2.11 (t, J=6.1 Hz, 2H), 2.46-2.51 (m, 1H), 4.04 (t, J=6.1 Hz, 2H), 4.88 (brs, 1H), 6.82 (d, J=8.3 Hz, 2H), 7.11 (d, J=8.3 Hz, 2H); $^{13}$C NMR (125.7 MHz, CDCl$_3$) δ 26.4, 26.8, 27.5 (br), 28.4, 31.6, 34.6, 34.7, 36.3, 36.7, 39.2 (br), 41.9, 51.7, 64.6, 78.5 (br), 108.3, 111.2, 114.2, 127.5, 138.3, 154.4 (br), 157.0. Step 5. A mixture of the above phenol ether (410 mg, 0.757 mmol) and p-toluenesulfonic acid monohydrate (3.10 g, 15 mmol) in THF (10 ml) was stirred at rt for 9 h, then cooled to 5° C., and alkalized with 0.5 M aq. NaOH to pH=12. After the THF was removed under vacuum, the water suspension was extracted with DCM (3×30 ml). The DCM layers were combined, washed with water (2×20 ml), dried over $Na_2SO_4$, and evaporated to give the desired free base. A mixture of the free base (350 mg, purity 80%, 0.637 mmol) and p-toluenesulfonic acid monohydrate (123 mg, 0.637 mmol) in ether (20 ml) was stirred at rt for 1 h. The precipitate was collected by filtration, washed with ether, and dried under vacuum to yield trioxolane OZ539 (340 mg, 73%) as a white powder. mp 152-153° C.; $^1$H NMR (500 MHz, CDCl$_3$) δ 1.38 (s, 6H), 1.61-2.03 (m, 22H), 2.07 (t, J=6.1 Hz, 2H), 2.32 (s, 3H), 2.41-2.50 (m, 1H), 3.98 (t, J=6.1

Hz, 2H), 6.73 (d, J=8.8 Hz, 2H), 7.01 (d, J=8.8 Hz, 2H), 7.11 (d, J=7.8 Hz, 2H), 7.74 (d, J=7.8 Hz, 2H), 7.86 (brs, 3H); $^{13}$C NMR (125.7 MHz, CDCl$_3$) δ 21.32, 25.76, 26.50, 26.89, 31.64, 34.74, 34.81, 36.41, 36.82, 38.75, 42.02, 54.25, 63.60, 108.40, 111.33, 114.39, 125.98, 127.51, 128.96, 138.51, 140.45, 141.51, 156.71. Anal. Calcd for C$_{34}$H$_{47}$NO$_7$S: C, 66.53; H, 7.72; N, 2.28. Found: C, 66.73; H, 7.90; N, 2.02.

cis-Adamantane-2-spiro-3'-8'-[4'-[2'-(tetrahydro-1',4'-oxazepin-4'(5'H)-yl)ethoxy]phenyl]-1',2',4'-trioxaspiro[4.5]decane p-tosylate (OZ543). A mixture of cis-adamantane-2-spiro-3'-8'-[4'-(2'-bromoethoxy)phenyl]-1',2',4'-trioxaspiro[4.5]decane (0.50 g, 1.08 mmol), homomorpholine hydrochloride (0.25 g, 1.82 mmol) and K$_2$CO$_3$ (2.00 g, 14.5 mmol) in dry acetonitrile (80 ml) was heated at 60° C. for 24 h. After the reaction mixture was cooled to rt, filtered to remove the solid material, the filtrate was concentrated. The residue was washed with water (50 ml) and dried in vacuo. The crude product (0.50 g) was dissolved in CH$_2$Cl$_2$ (5 ml) and then a solution of p-toluenesulfonic acid monohydrate (0.20 g, 1.1 mmol) in ethyl acetate (20 ml) was added. The precipitate was collected by filtration to afford trioxolane OZ543 (0.51 g, 72%) as a colorless solid. mp 140-141° C.; $^1$H NMR (500 MHz, CDCl$_3$) δ 1.54-2.16 (m, 23H), 2.37 (s, 3H), 2.46-2.54 (m, 1H), 2.56-2.69 (m, 1H), 3.16-3.26 (m, 1H), 3.32-3.42 (m, 1H), 3.59-3.68 (m, 2H), 3.72-4.08 (m, 6H), 4.37-4.44 (m, 2H), 6.76 (d, J=8.0 Hz, 2H), 7.11 (d, J=8.0 Hz, 2H), 7.18 (d, J=7.5 Hz, 2H), 7.77 (d, J=7.5 Hz, 2H), 11.31 (br, s, 1H); $^{13}$C NMR (125.7 MHz, CDCl$_3$) δ 21.35, 25.35, 26.48, 26.88, 31.59, 34.68, 34.80, 36.41, 36.79, 42.04, 53.89, 56.68, 58.02, 63.02, 63.27, 67.28, 108.32, 111.44, 114.42, 125.90, 127.93, 128.89, 139.93, 140.25, 141.93, 155.40.

cis-Adamantane-2-spiro-3'-8'-[4'-[(trans-4'-aminocyclohexyl)methoxy]phenyl]-1',2',4'-trioxaspiro[4.5]decane mesylate (OZ545). Step 1. To a stirred solution of trans-4-aminocyclohexanecarboxylic acid methyl ester hydrochloride (1.0 g, 5.17 mmol) and triethylamine (2 ml) in CH$_2$Cl$_2$ (30 ml) was added Boc$_2$O (1.20 g, 5.50 mmol). The resulting mixture was stirred at rt overnight. After removal of the solvent, the residue was washed with water (30 ml) and dried in vacuo to give trans-4-(tert-butoxycarbonylamino)cyclohexanecarboxylic acid methyl ester (1.10 g, 83%) as a colorless solid. mp 80-81° C.; $^1$H NMR (500 MHz, CDCl$_3$) δ 1.05-1.16 (m, 2H), 1.46-1.58 (m, 2H), 1.44 (s, 9H), 1.97-2.11 (m, 4H), 2.18-2.27 (m, 1H), 3.41 (brs, 1H), 3.66 (s, 3H), 4.38 (brs, 1H); $^{13}$C NMR (125.7 MHz, CDCl$_3$) δ 27.79, 28.39, 32.53, 42.35, 48.95, 51.63, 79.22, 155.13, 175.86. Step 2. To a solution of trans-4-(tert-butoxycarbonylamino)cyclohexanecarboxylic acid methyl ester (1.00 g, 3.89 mmol) in ether (40 ml) and THF (8 ml) was added dropwise 2 M lithium borohydride in THF (1.95 ml, 3.89 mmol) followed by 1 M lithium triethylborohydride in THF (0.40 ml, 0.39 mmol). The resulting mixture was stirred at rt for 24 h and then diluted with ether (30 ml). The mixture was washed with 2 M aq. NaOH (2×5 ml), water (2×5 ml) and brine (5 ml), dried over MgSO$_4$, filtered, and concentrated to afford tert-butyl trans-(4-hydroxymethyl)cyclohexylcarbamate as a colorless solid (0.89 g, 99%). mp 124-125° C. $^1$H NMR (500 MHz, CDCl$_3$) δ 1.00-1.15 (m, 2H), 1.44 (s, 9H), 1.50-1.64 (m, 2H), 1.79-1.86 (m, 2H), 2.02-2.08 (m, 2H), 3.39 (brs, 1H), 3.46 (d, J=6.0 Hz, 2H), 4.39 (brs, 1H); $^{13}$C NMR (125.7 MHz, CDCl$_3$) δ 28.18, 28.40, 32.89, 39.58, 49.84, 68.06, 79.07, 155.20. Step 3. Diisopropyl azodicarboxylate (0.69 ml, 3.24 mmol) was added dropwise to a mixture of OZ288 (1.00 g, 2.80 mmol), tert-butyl trans-(4-hydroxymethyl)cyclohexylcarbamate (0.64 g, 2.80 mmol), and triphenylphosphine (0.85 g, 3.24 mmol) in THF (50 ml) at 0° C. under Ar. The resulting mixture was stirred at rt for 24 h. After removal of the solvent, the crude product was purified by crystallization from EtOH to afford the desired BOC derivative (0.52 g, 33%) as a colorless solid. mp 157-158° C.; $^1$H NMR (500 MHz, CDCl$_3$) δ 1.07-1.20 (m, 2H), 1.44 (s, 9H), 1.64-2.10 (m, 29H), 2.44-2.54 (m, 1H), 3.42 (brs, 1H), 3.72 (d, J=6.0 Hz, 2H), 4.39 (brs, 1H), 6.80 (d, J=9.0 Hz, 2H), 7.10 (d, J=9.0 Hz, 2H); $^{13}$C NMR (125.7 MHz, CDCl$_3$) δ 26.46, 26.87, 28.42, 28.54, 31.65, 32.90, 34.74, 34.79, 36.38, 36.79, 36.93, 42.04, 49.79, 72.78, 79.11, 108.45, 111.36, 114.26, 127.58, 138.22, 155.20, 157.43. Step 4. A mixture of the BOC derivative (0.40 g, 0.71 mmol) and MsOH (1.5 M in THF, 12 ml, 180 mol) was stirred at rt for 4 h. The resulting precipitate was filtered off, washed with ether (30 ml), and dried in vacuo to afford trioxolane OZ545 (0.32 g, 81%) as a colorless solid. mp 168-169° C.; $^1$H NMR (500 MHz, CDCl$_3$) δ 1.11-1.27 (m, 2H), 1.45-1.59 (m, 2H), 1.64-2.25 (m, 27H), 2.44-2.54 (m, 1H), 2.80 (s, 3H), 3.04-3.16 (m, 1H), 3.73 (d, J=6.0 Hz, 2H), 6.79 (d, J=9.0 Hz, 2H), 7.10 (d, J=9.0 Hz, 2H), 7.61 (brs, 3H); $^{13}$C NMR (125.7 MHz, CDCl$_3$) δ 26.48, 26.88, 27.65, 30.20, 31.65, 34.74, 34.80, 36.40, 36.80, 42.04, 72.24, 108.44, 111.36, 114.29, 127.62, 138.39, 157.30.

EXAMPLE 4

Embryotoxicity Data

Several 1,2,4-trioxolanes (OZ) were tested in the rat whole embryo culture (WEC) model (Longo et al., 2006) and were found to affect development in a manner similar to that of dihydroartemisinin and artemisinin, although the non observed adverse effect levels (NOAELs) were significantly higher for the newer OZ compounds compared to OZ277. Embryonic red blood cells (RBCs) were the primary target leading to anemia and subsequent hypoxia in embryonic tissues. The NOAEL for embryonic RBCs was 0.01 μg/mL for dihydroartemisinin, 0.1 μg/mL for artemisinin, and 0.2 μg/mL for OZ277, whereas it was considerably higher for the newer OZ compounds (5 μg/mL for OZ439, and 1 μg/mL for OZ493).

Longo, M.; Zanoncelli, S.; Manera, D.; Brughera, M.; Colombo, P.; Lansen J.; Mazué, G.; Gomes, M.; Taylor W. R. J.; Olliaro, P. Effects of the Antimalarial Drug Dihydroartemisinin (DHA) on Rat Embryos In Vitro. Repro. Tox. 2006, 21, 83-93.

It should be appreciated that the spiro and dispiro 1,2,4-trioxolane compositions of this invention may contain trioxolanes within the scope of the formulas described above, or prodrugs or analogues of these compounds or a racemic mixture of either the D or the L form. The invention is also intended to include all biologically active salt forms of the compounds. Also, minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:
1. A dispiro 1,2,4-trioxolane selected from the group consisting of
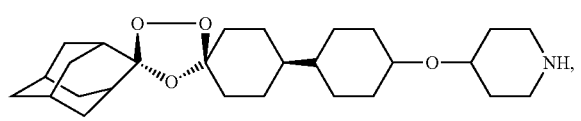
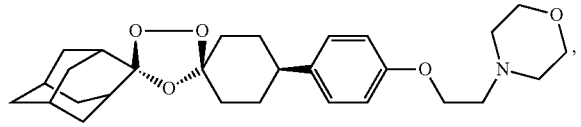
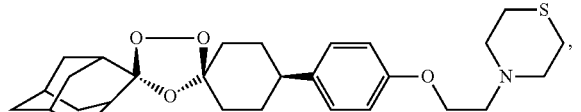
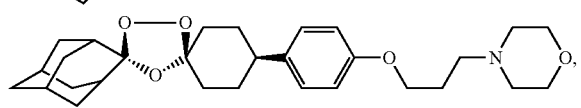
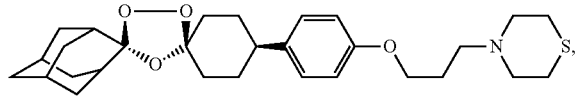
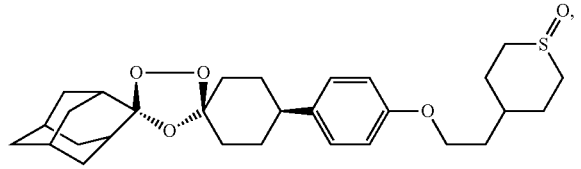
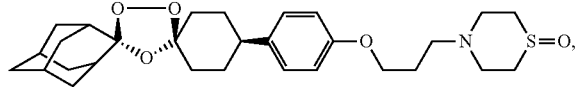
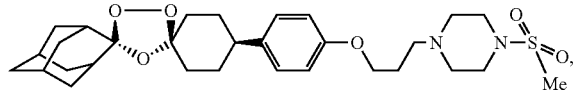
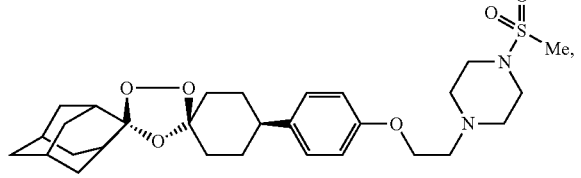
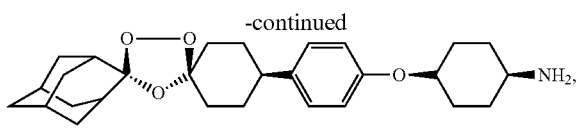
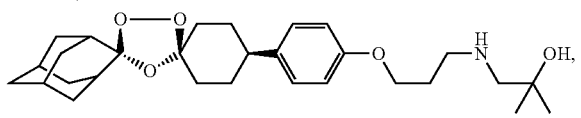
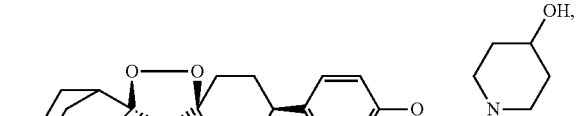
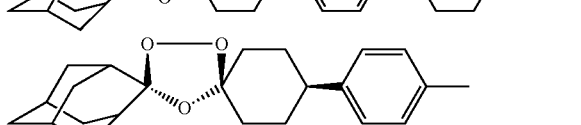
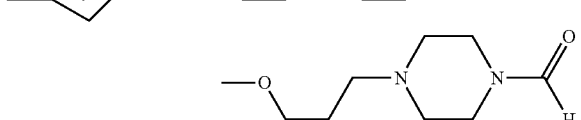
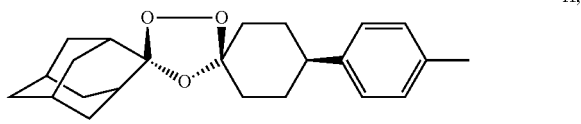
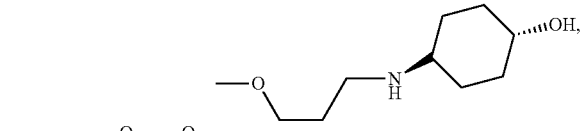
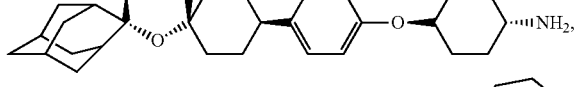
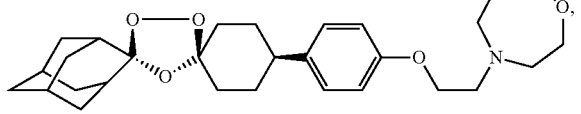
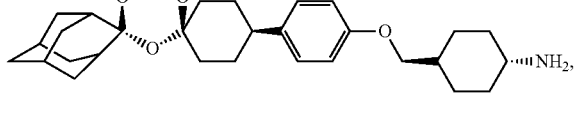
and diasteromeric forms thereof.
2. The dispiro 1,2,4-trioxolane of claim 1 selected from the group consisting of
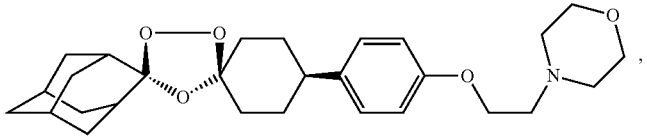
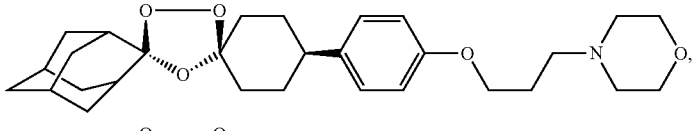
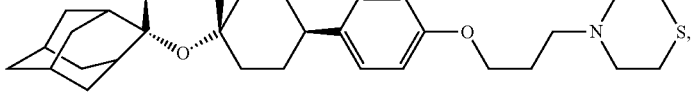

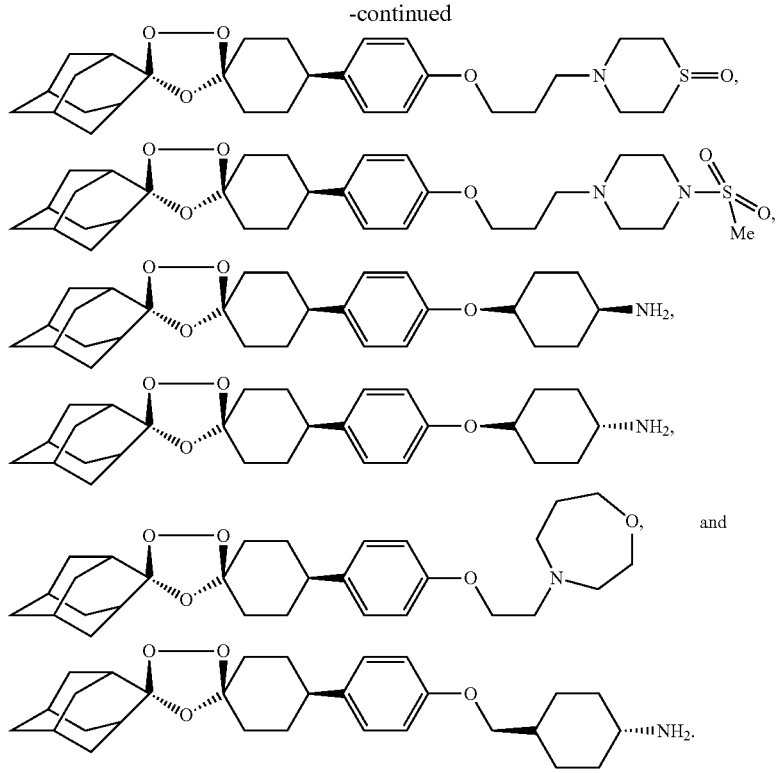

3. The dispiro 1,2,4-trioxolane of claim 1 further including a pharmaceutically acceptable carrier.

4. A method of reducing the incidence of or treating malaria comprising:

administrating a malaria incidence reducing or malaria treatment effective amount of a dispiro 1,2,4-trioxolane in a pharmaceutically acceptable carrier, said trioxolane being selected from the group consisting of

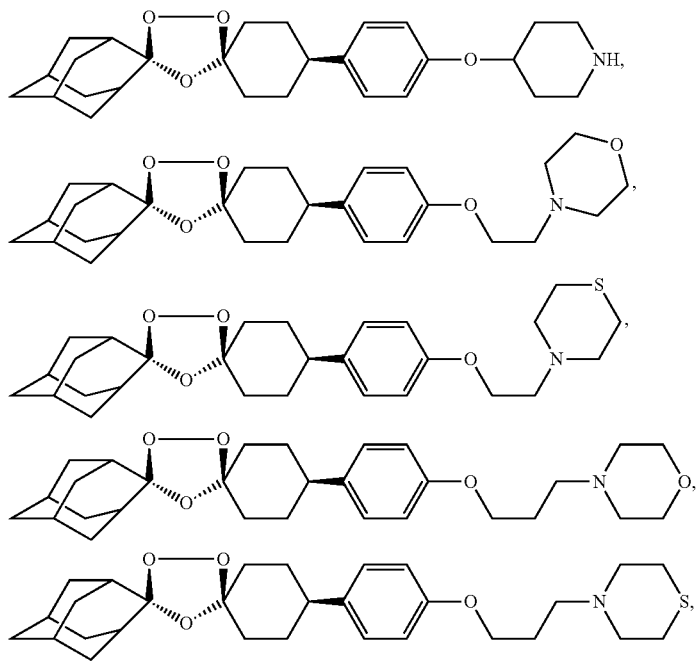

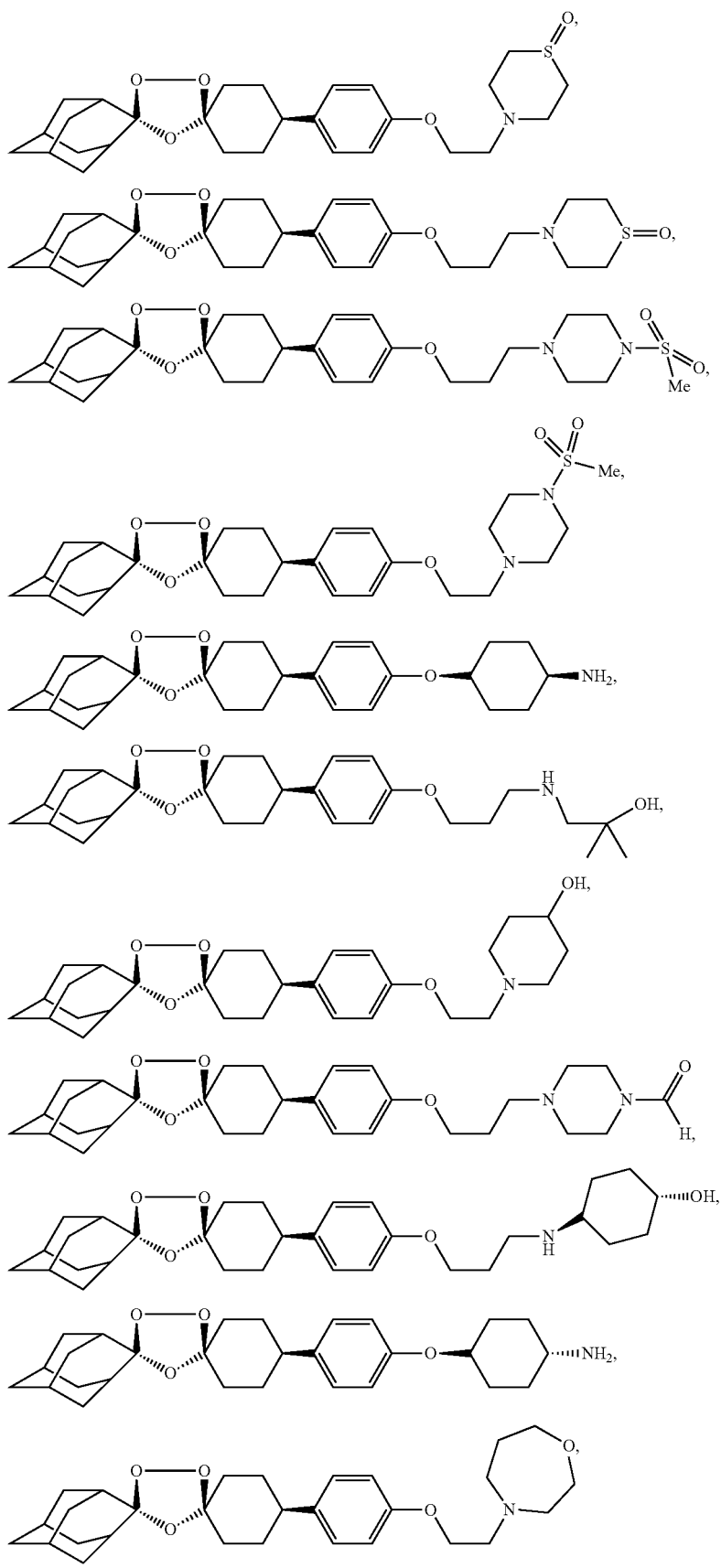

-continued

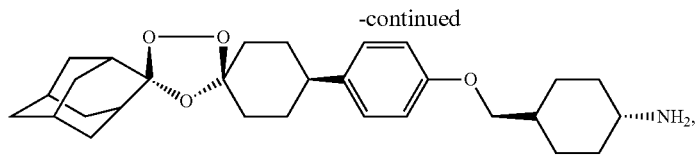

and diasteromeric forms thereof.

5. The method of claim 4 whereby the trioxolane is administered as a single dose.

6. The method of claim 5 whereby the trioxolane is administered before or after exposure to malaria.

7. The method of claim 5 whereby the trioxolane is administered in a dosing range of from about 0.5-5.0 mg/kg.

8. The method of claim 4 whereby the trioxolane is administered more than once in a dose ranging from about 0.1-1000 mg/kg/day.

9. The method of claim 7 whereby the trioxolane is administered in a dose ranging from about 1-100 mg/kg/day.

10. The method of claim 7 whereby the trioxolane is administered in a pharmaceutically effective salt form.

11. The method of claim 10 whereby the salt is selected from the group consisting of acetate, adipate, alginate, citrate, aspartate, benzoate, benzene sulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene, sulfonate, oxalate, palmitoate, pectinate, persulfate, 3-phenylpropionate, picrate, pivalate, propionate, succinate, tartrate, thiocyanate, phosphate, glutamate, bicarbonate, p-toluene sulfonate and undecanoate salt.

12. The method of claim 7 whereby the trioxolane is administered with another antimalarial as part of a combination therapy.

13. The method of claim 7 whereby the trioxolane is administered orally.

14. A method of manufacturing a composition comprising: mixing an amount of a dispiro 1,2,4-trioxolane sufficient to decrease the likehood of infection and subsequent disease by malarial parasites or a malaria treatment-effective amount of said dispiro 1,2,4-trioxolane, with a pharmaceutically acceptable carrier, said trioxolane being selected from the group consisting of

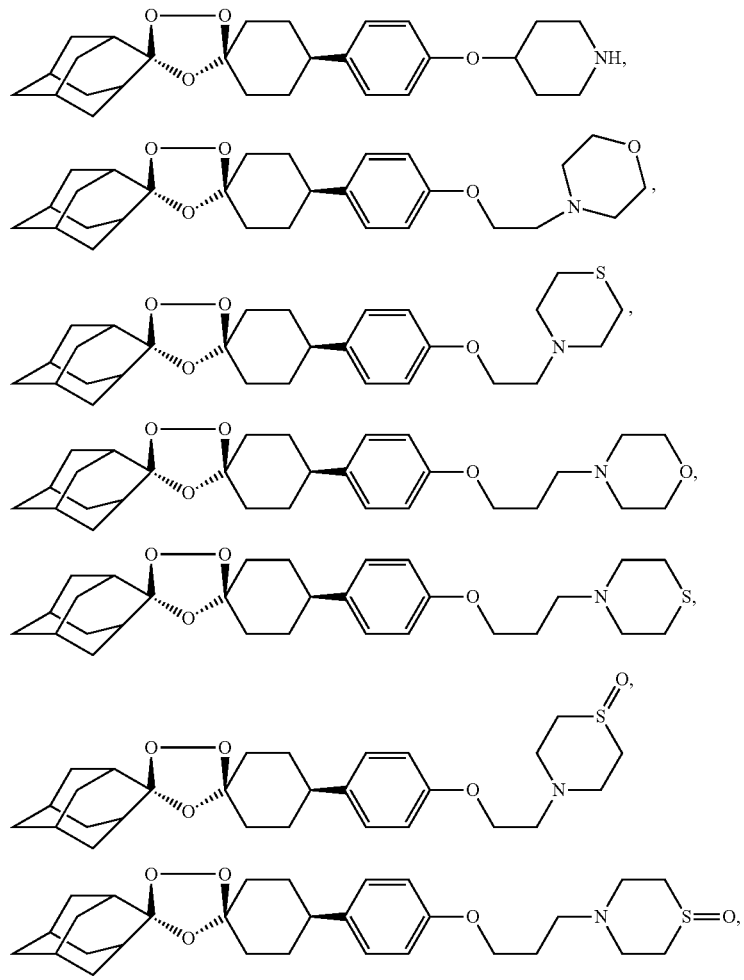

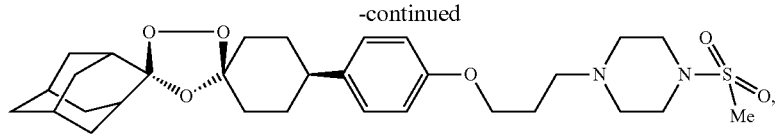
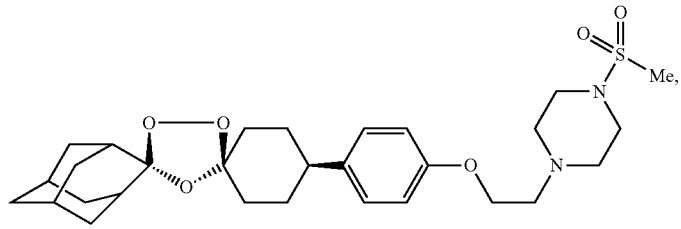
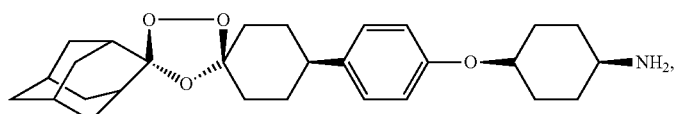
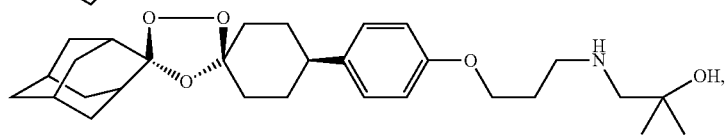
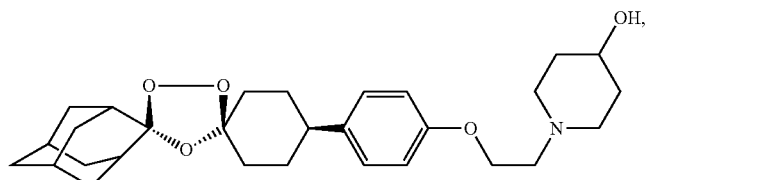
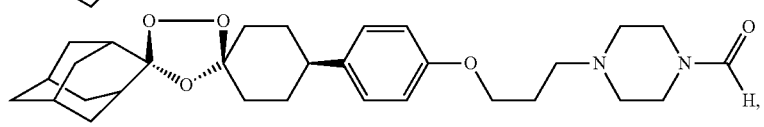
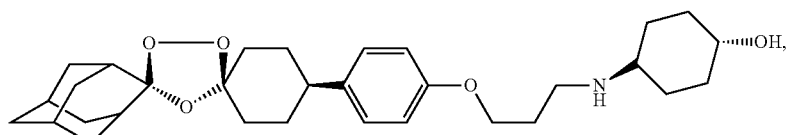
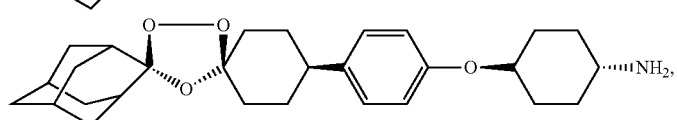
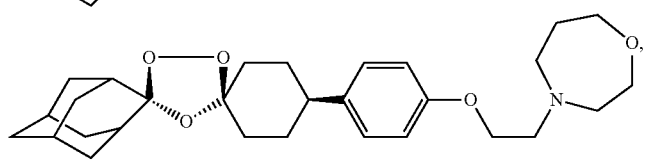
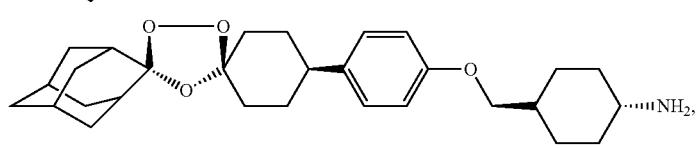
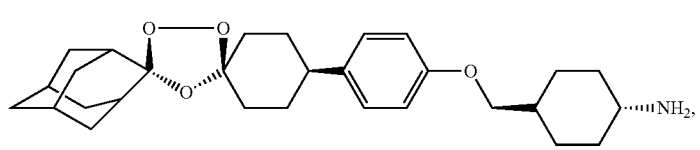
and diastereomeric forms thereof.

15. A method of reducing the incidence of or treating schistosomiasis comprising: administrating a schistosomiasis treatment effective amount of a dispiro 1,2,4-trioxolane in a pharmaceutically acceptable carrier, said trioxolane being selected from the group consisting of:
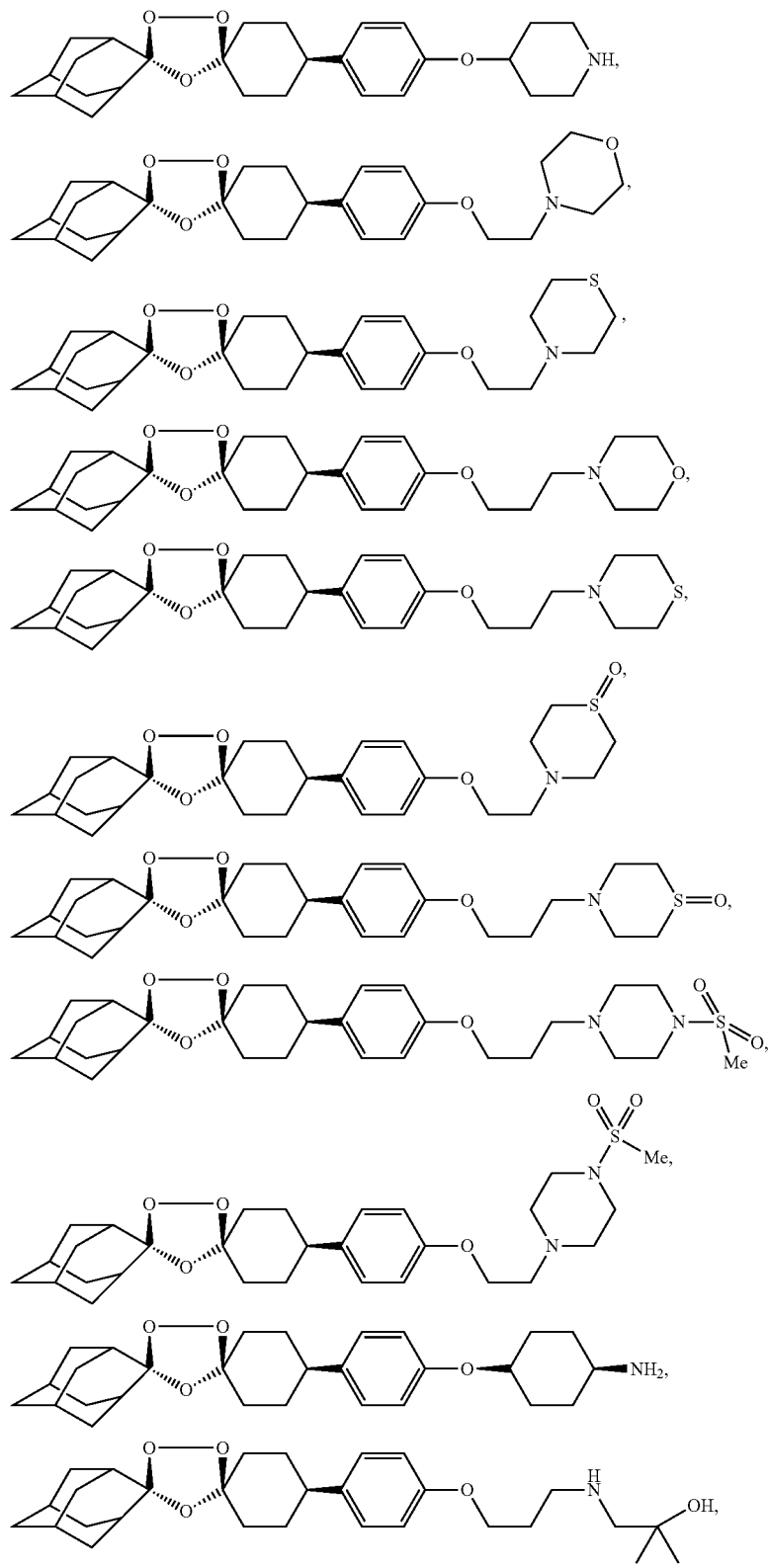

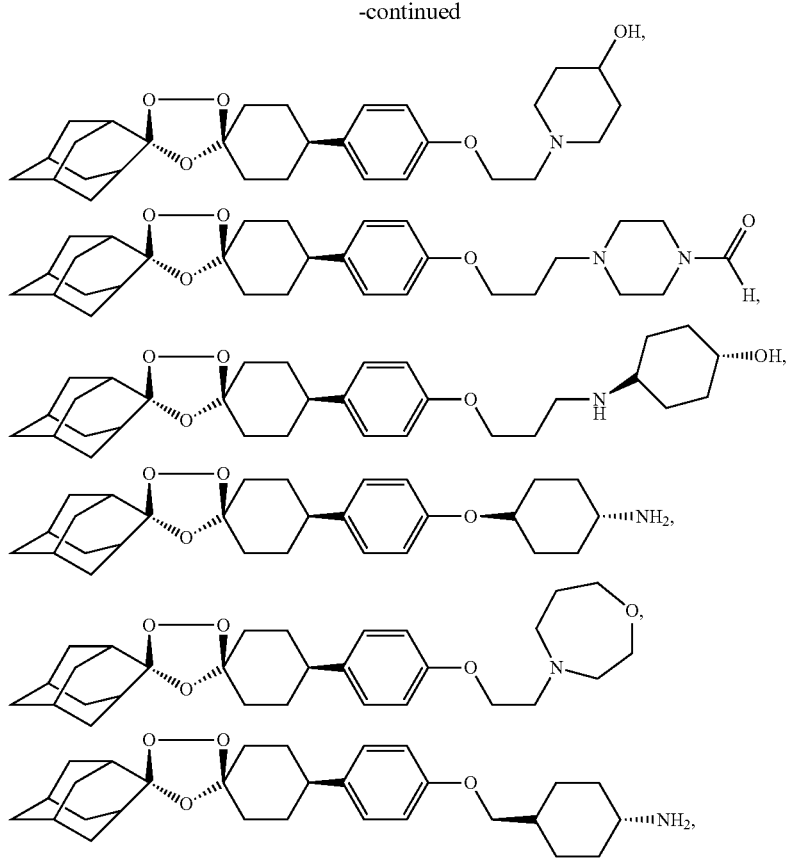

and diasteromeric forms thereof.

16. The dispiro 1,2,4-trioxolane of claim 1 as a pharmaceutically effective salt form.

17. The dispiro 1,2,4-trioxolane of claim 16, wherein the salt is selected from the group consisting of acetate, adipate, alginate, citrate, aspartate, benzoate, benzene sulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluene sulfonate and undecanoate salt.

18. The dispiro 1,2,4-trioxolane of claim 17 wherein the dispiro 1,2,4-trioxolane is cisAdamantane-2-spiro-3'-8'-[4'-[2'-(4'-morpholinyl)ethoxy]phenyl]-1',2',4'-trioxaspiro[4.5]decane mesylate.

* * * * *

UNITED STATES PATENT AND TRADEMARK OFFICE
CERTIFICATE OF CORRECTION

PATENT NO. : 8,067,620 B2
APPLICATION NO. : 11/930606
DATED : November 29, 2011
INVENTOR(S) : Jonathan L. Vennerstrom et al.

It is certified that error appears in the above-identified patent and that said Letters Patent is hereby corrected as shown below:

In Claim 1, at column 29, line 30, the "N" was omitted from the end of the chain. The correct sixth compound in Claim 1, at column 29, line 30, should read as follows:

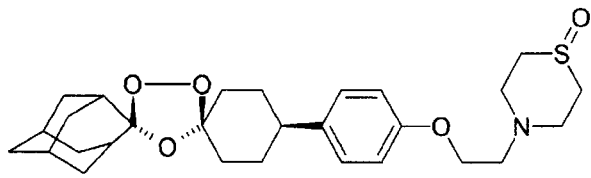

In Claim 1, at column 30, lines 17-24, a single structure was shown in two parts. The correct thirteenth compound should read as follows:

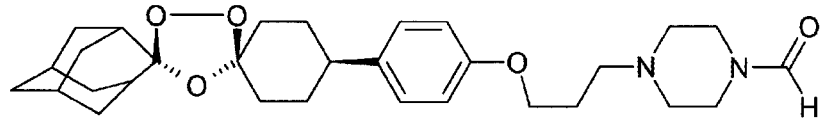

In Claim 1, at column 30, lines 24-34, a single structure was shown in two parts. The correct fourteenth compound should read as follows:

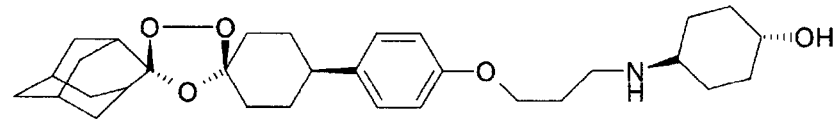

In Claim 18, at column 42, line 41, please add a "-" between "cis" and "Adamantane" and at the end of line 42 of column 42, please replace the "." in "[4.5]" with a "," "[4,5]" so the chemical name appears correctly as "cis-Adamantane-2-spiro-3'-8'-[4'-[2'-(4'-morpholinyl)ethoxy]phenyl]-1',2',4'-trioxaspiro[4,5]decane mesylate."

Signed and Sealed this
Twenty-sixth Day of March, 2013

Teresa Stanek Rea
*Acting Director of the United States Patent and Trademark Office*